United States Patent
Dimitrov et al.

(10) Patent No.: US 9,914,966 B1
(45) Date of Patent: Mar. 13, 2018

(54) APPARATUS AND METHODS FOR ANALYSIS OF BIOMOLECULES USING HIGH FREQUENCY ALTERNATING CURRENT EXCITATION

(71) Applicant: Nabsys 2.0 LLC, Providence, RI (US)

(72) Inventors: Valentin Dimitrov, Providence, RI (US); Nathan Weiner, Upton, MA (US)

(73) Assignee: NABSYS 2.0 LLC, Providence, RI (US)

( * ) Notice: Subject to any disclaimer, the term of this patent is extended or adjusted under 35 U.S.C. 154(b) by 821 days.

(21) Appl. No.: 14/105,391

(22) Filed: Dec. 13, 2013

Related U.S. Application Data

(60) Provisional application No. 61/740,146, filed on Dec. 20, 2012.

(51) Int. Cl.
| | | |
|---|---|---|
| *G01N 27/447* | (2006.01) | |
| *C12Q 1/68* | (2018.01) | |
| *G01N 33/487* | (2006.01) | |
| *G01N 27/414* | (2006.01) | |

(52) U.S. Cl.
CPC ....... *C12Q 1/6874* (2013.01); *G01N 27/4145* (2013.01); *G01N 33/48721* (2013.01); *G01N 27/447* (2013.01)

(58) Field of Classification Search
None
See application file for complete search history.

(56) References Cited

U.S. PATENT DOCUMENTS

| | | |
|---|---|---|
| 3,699,437 A | 10/1972 | Ur |
| H201 H | 1/1987 | Yager |
| 4,810,650 A | 3/1989 | Kell et al. |
| 4,874,499 A | 10/1989 | Smith et al. |
| 5,194,133 A | 3/1993 | Clark et al. |
| 5,202,231 A | 4/1993 | Drmanac et al. |
| 5,246,552 A | 9/1993 | Kamiya et al. |
| 5,314,829 A | 5/1994 | Coles |
| 5,405,519 A | 4/1995 | Schwartz |
| 5,427,663 A | 6/1995 | Austin et al. |
| 5,455,166 A | 10/1995 | Walker |
| 5,539,082 A | 7/1996 | Nielsen et al. |

(Continued)

FOREIGN PATENT DOCUMENTS

| | | |
|---|---|---|
| DE | 19936302 A1 | 2/2001 |
| EP | 455508 A1 | 11/1991 |

(Continued)

OTHER PUBLICATIONS

"About Lock-In Amplifiers" (Stanford Research), last modified Jan. 19, 2004 and accessed Mar. 29, 2016 at http://www.thinksrs.com/downloads/PDFs/ApplicationNotes/AboutLIAs.pdf.*

(Continued)

*Primary Examiner* — Luan V Van
*Assistant Examiner* — Steven E Rosenwald
(74) *Attorney, Agent, or Firm* — Goodwin Procter LLP

(57) ABSTRACT

The invention relates to devices and methods for hybridization assisted sequencing of biomolecule analytes in nanopores, nano-channels and micro-channels. An alternating current signal may be employed to achieve a significantly improved signal-to-noise ratio, thereby enhancing system performance.

34 Claims, 21 Drawing Sheets

(56) References Cited

U.S. PATENT DOCUMENTS

| | | |
|---|---|---|
| 5,560,811 A | 10/1996 | Briggs et al. |
| 5,599,664 A | 2/1997 | Schwartz |
| 5,650,305 A | 7/1997 | Hui et al. |
| 5,681,947 A | 10/1997 | Bergstrom et al. |
| 5,683,881 A | 11/1997 | Skiena |
| 5,720,928 A | 2/1998 | Schwartz |
| 5,744,366 A | 4/1998 | Kricka et al. |
| 5,773,571 A | 6/1998 | Nielsen et al. |
| 5,795,782 A | 8/1998 | Church et al. |
| 5,824,477 A | 10/1998 | Stanley |
| 5,837,115 A | 11/1998 | Austin et al. |
| 5,908,745 A | 6/1999 | Mirzabekov et al. |
| 5,928,869 A | 7/1999 | Nadeau et al. |
| 5,942,391 A | 8/1999 | Zhang et al. |
| 5,972,619 A | 10/1999 | Drmanac et al. |
| 6,015,714 A | 1/2000 | Baldarelli et al. |
| 6,020,599 A | 2/2000 | Yeo |
| 6,025,891 A | 2/2000 | Kim |
| 6,084,648 A | 7/2000 | Yeo |
| 6,096,503 A | 8/2000 | Sutcliffe et al. |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,270,965 B1 | 8/2001 | Kleiber et al. |
| 6,274,320 B1 | 8/2001 | Rothberg et al. |
| 6,294,136 B1 | 9/2001 | Schwartz |
| 6,303,288 B1 | 10/2001 | Furcht et al. |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,410,243 B1 | 6/2002 | Wyrick et al. |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 | 10/2002 | Golovchenko et al. |
| 6,497,138 B1 | 12/2002 | Abdel-Rahman et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,706,203 B2 | 3/2004 | Barth et al. |
| 6,713,263 B2 | 3/2004 | Schwartz |
| 6,723,513 B2 | 4/2004 | Lexow |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,887,714 B2 | 5/2005 | Fritsch et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 6,952,651 B2 | 10/2005 | Su |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,257,987 B2 | 8/2007 | O'Brien et al. |
| 7,259,342 B2 | 8/2007 | Lin et al. |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,468,271 B2 | 12/2008 | Golovchenko et al. |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,625,706 B2 | 12/2009 | Akeson et al. |
| 7,670,770 B2 | 3/2010 | Chou et al. |
| 7,678,562 B2 | 3/2010 | Ling |
| 7,731,826 B2 | 6/2010 | Hibbs et al. |
| 7,744,816 B2 | 6/2010 | Su et al. |
| 7,824,859 B2 | 11/2010 | Sorge |
| 7,854,435 B2 | 12/2010 | Campbell |
| 7,867,782 B2 | 1/2011 | Barth |
| 7,897,344 B2 | 3/2011 | Dahl et al. |
| 7,939,259 B2 | 5/2011 | Kokoris et al. |
| 8,003,319 B2 | 8/2011 | Polonsky et al. |
| 8,133,719 B2 | 3/2012 | Drmanac et al. |
| 8,206,568 B2 | 6/2012 | Branton et al. |
| 8,232,055 B2 | 7/2012 | Bruhn et al. |
| 8,232,582 B2 | 7/2012 | Sauer et al. |
| 8,246,799 B2 | 8/2012 | Oliver et al. |
| 8,262,879 B2 | 9/2012 | Oliver |
| 8,278,047 B2 | 10/2012 | Oliver et al. |
| 8,278,050 B2 | 10/2012 | Bailey et al. |
| 8,333,934 B2 | 12/2012 | Cao et al. |
| 8,455,260 B2 | 6/2013 | Goldstein et al. |
| 8,507,197 B2 | 8/2013 | Palaniappan |
| 8,574,892 B2 | 11/2013 | Su |
| 8,592,182 B2 | 11/2013 | Kokoris et al. |
| 8,628,919 B2 | 1/2014 | Xiao et al. |
| 8,715,933 B2 | 5/2014 | Oliver |
| 8,882,980 B2 | 11/2014 | Ling et al. |
| 8,926,813 B2 | 1/2015 | Oliver |
| 2002/0028458 A1 | 3/2002 | Lexow |
| 2002/0061588 A1 | 5/2002 | Jacobson et al. |
| 2002/0108136 A1 | 8/2002 | Pati et al. |
| 2002/0127855 A1 | 9/2002 | Sauer et al. |
| 2002/0150961 A1 | 10/2002 | Bogyo et al. |
| 2003/0003609 A1 | 1/2003 | Sauer et al. |
| 2003/0064095 A1 | 4/2003 | Martin et al. |
| 2003/0104428 A1 | 6/2003 | Branton et al. |
| 2003/0143614 A1 | 7/2003 | Drmanac |
| 2003/0186256 A1 | 10/2003 | Fischer |
| 2004/0137734 A1 | 7/2004 | Chou et al. |
| 2004/0146430 A1 | 7/2004 | Dugas |
| 2005/0019784 A1 | 1/2005 | Su et al. |
| 2005/0202444 A1* | 9/2005 | Zhu .................... C12Q 1/6825 435/6.12 |

(56) References Cited

U.S. PATENT DOCUMENTS

| | | | |
|---|---|---|---|
| 2006/0057025 A1* | 3/2006 | Eversmann | G01N 27/4145 422/82.02 |
| 2006/0194306 A1* | 8/2006 | Herr | B82Y 10/00 435/287.2 |
| 2006/0269483 A1 | 11/2006 | Austin et al. | |
| 2006/0287833 A1 | 12/2006 | Yakhini | |
| 2007/0039920 A1 | 2/2007 | Kutchoukov et al. | |
| 2007/0042366 A1 | 2/2007 | Ling | |
| 2007/0054276 A1 | 3/2007 | Sampson | |
| 2007/0084163 A1 | 4/2007 | Lai | |
| 2007/0178240 A1 | 8/2007 | Yamazaki et al. | |
| 2007/0190524 A1 | 8/2007 | Mauclere et al. | |
| 2007/0190542 A1 | 8/2007 | Ling et al. | |
| 2007/0218471 A1 | 9/2007 | Kim et al. | |
| 2007/0238112 A1* | 10/2007 | Sohn | B01L 3/502761 435/6.19 |
| 2008/0085840 A1 | 4/2008 | Buzby | |
| 2008/0119366 A1 | 5/2008 | Sauer et al. | |
| 2008/0242556 A1 | 10/2008 | Cao et al. | |
| 2008/0254995 A1 | 10/2008 | Kim et al. | |
| 2008/0305482 A1 | 12/2008 | Brentano et al. | |
| 2009/0005252 A1 | 1/2009 | Drmanac et al. | |
| 2009/0011943 A1 | 1/2009 | Drmanac et al. | |
| 2009/0099786 A1 | 4/2009 | Oliver et al. | |
| 2009/0111115 A1 | 4/2009 | Drmanac et al. | |
| 2009/0136948 A1 | 5/2009 | Han et al. | |
| 2009/0214392 A1 | 8/2009 | Kameoka et al. | |
| 2009/0299645 A1 | 12/2009 | Colby et al. | |
| 2010/0096268 A1* | 4/2010 | Ling | B82Y 15/00 204/549 |
| 2010/0143960 A1 | 6/2010 | Bazin | |
| 2010/0203076 A1 | 8/2010 | Fotin-Mleczek et al. | |
| 2010/0214162 A1 | 8/2010 | Talbot et al. | |
| 2010/0243449 A1 | 9/2010 | Oliver | |
| 2010/0297644 A1 | 11/2010 | Kokoris et al. | |
| 2010/0310421 A1 | 12/2010 | Oliver et al. | |
| 2012/0052079 A1 | 3/2012 | Richardson et al. | |
| 2012/0074925 A1 | 3/2012 | Oliver | |
| 2012/0208193 A1 | 8/2012 | Okino et al. | |
| 2012/0214162 A1 | 8/2012 | Oliver | |
| 2012/0222958 A1* | 9/2012 | Pourmand | B01L 3/021 204/451 |
| 2013/0011934 A1 | 1/2013 | Oliver et al. | |
| 2014/0087390 A1 | 3/2014 | Oliver et al. | |
| 2014/0174927 A1 | 6/2014 | Bashir et al. | |
| 2014/0212874 A1 | 7/2014 | Oliver | |
| 2014/0224356 A1 | 8/2014 | Hatton et al. | |

FOREIGN PATENT DOCUMENTS

| | | | |
|---|---|---|---|
| EP | 0958495 A1 | 11/1999 | |
| EP | 1486775 A1 | 12/2004 | |
| EP | 1685407 A1 | 8/2006 | |
| JP | 2002526759 A | 8/2002 | |
| JP | 2003-028826 A | 1/2003 | |
| JP | 2003510034 A | 3/2003 | |
| JP | 2003513279 A | 4/2003 | |
| JP | 2004004064 A | 1/2004 | |
| JP | 2007068413 A | 3/2007 | |
| WO | WO-1990004652 A1 | 5/1990 | |
| WO | WO-1993022678 A2 | 11/1993 | |
| WO | WO-1996017957 A1 | 6/1996 | |
| WO | WO-1998035012 A2 | 8/1998 | |
| WO | WO-2000009757 A1 | 2/2000 | |
| WO | WO-2000011220 A1 | 3/2000 | |
| WO | WO-2000020626 A1 | 4/2000 | |
| WO | WO-2000022171 A2 | 4/2000 | |
| WO | WO-0056937 A2 | 9/2000 | |
| WO | WO-2000062931 A1 | 10/2000 | |
| WO | WO-0079257 A1 | 12/2000 | |
| WO | WO-2001018246 A1 | 3/2001 | |
| WO | WO-2001031063 A1 | 5/2001 | |
| WO | WO-2001033216 A1 | 5/2001 | |
| WO | WO-2001037958 A2 | 5/2001 | |
| WO | WO-2001042782 A1 | 6/2001 | |
| WO | WO-2001046467 A2 | 6/2001 | |
| WO | WO-2002007199 A1 | 1/2002 | |
| WO | WO-2002050534 | 6/2002 | |
| WO | WO-02066595 A1 | 8/2002 | |
| WO | WO-2003000920 A2 | 1/2003 | |
| WO | WO-2003010289 A2 | 2/2003 | |
| WO | WO-2003079416 A1 | 9/2003 | |
| WO | WO-2003089666 A2 | 10/2003 | |
| WO | WO-2003106693 A2 | 12/2003 | |
| WO | WO-2004035211 A1 | 4/2004 | |
| WO | WO-2004085609 A2 | 10/2004 | |
| WO | WO-2005017025 A2 | 2/2005 | |
| WO | WO-2006020775 A2 | 2/2006 | |
| WO | WO-2006028508 A2 | 3/2006 | |
| WO | WO-2006052882 A1 | 5/2006 | |
| WO | WO-2007021502 A1 | 2/2007 | |
| WO | WO-2007041621 A2 | 4/2007 | |
| WO | WO-2007084076 A1 | 7/2007 | |
| WO | WO-2007106509 A2 | 9/2007 | |
| WO | WO-2007109228 A1 | 9/2007 | |
| WO | WO-2007111924 A2 | 10/2007 | |
| WO | WO-2007127327 A2 | 11/2007 | |
| WO | WO-2008021488 A1 | 2/2008 | |
| WO | WO-2008039579 A2 | 4/2008 | |
| WO | WO-2008042018 A2 | 4/2008 | |
| WO | WO-2008046923 A2 | 4/2008 | |
| WO | WO-2008049021 A2 | 4/2008 | |
| WO | WO-2008069973 A2 | 6/2008 | |
| WO | WO-2008079169 A2 | 7/2008 | |
| WO | WO-2009046094 A1 | 4/2009 | |
| WO | WO-2010002883 A2 | 1/2010 | |
| WO | WO-2010111605 A2 | 9/2010 | |
| WO | WO-2010138136 A1 | 12/2010 | |
| WO | WO-2011109825 A2 | 9/2011 | |
| WO | WO-2012109574 A2 | 8/2012 | |
| WO | WO-2013016486 A1 | 1/2013 | |
| WO | WO-2014052433 A2 | 4/2014 | |

OTHER PUBLICATIONS

Akeson, et al., "Microsecond time-scale discrimination among polycytidylic acid, polyadenylic; acid, and polyuridylic acid as homopolymers or as segments within single RNA molecules,"; Biophys. J. 77, 3227-3233 (1999).

Alberts, B., et al., (1970) "T4 Bacteriophage Gene 32: A Structural Protein in the Replication and Recombination of DNA," Nature 227:1313-1318.

Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.

Anderson, P. et al., "Nkx3.1 and Myc crossregulate shared target genes in mouse and human prostate tumorigenesis," J. Clinical Investigation, May 2012, pp. 1907-1919, vol. 122, http://www.jci.org.

Arratia, R., et al., (1989) "Poisson Process Approximation for Repeats in One Sequence and Its Application to Sequencing by Hybridization," Dept. of Mathematics, University of Southern California.

Arrowsmith, C. et al., "Epigenetic protein families: a new frontier for drug discovery," Nature Reviews: Drug Discovery, May 2012, pp. 384-400, vol. 11, Macmillan Publishers Limited.

Ashkin, "Optical trapping and manipulation of neutral particles using lasers," Proc. Natl.; Acad. Sci. USA, vol. 94, DD. 4853-4860, May 1997.

Austin, M., et al., (2004) "Fabrication of 5 nm Linewidth and 14 nm Pitch Features by Nanoimprint Lithography," App. Phys. Lett. 84:5299-5301.

Austin, Robert, "The art of sucking spaghetti", Nature Publishing Group, Nature Materials, vol. 2, pp. 567-568, Sep. 2003.

Bains, W., et al., (1988) "A Novel Method for Nucleic Acid Sequence Determination," J. Theor. Biol. 135:303-307.

(56) References Cited

OTHER PUBLICATIONS

Baliga, R. et al., (2001) "Kinetic Consequences of Covalent Linkage of DNA Binding Polyamides," Biochemistry 40:3-8.
Ben-Dor et al, "On the Complexity of Positional Sequencing by Hybridization", Journal of Computational Biology, vol. 8, No. 4, 2001, pp. 361-371.
Bennett et al., (2005) "Toward the $1000 Human Genome," Pharmacogenomics 6:373-382.
Bianco, P. et al., "Interaction of the RecA Protein of *Escherichia coli* with Single-Stranded Oligodeoxyribonucleotides," Nucleic Acids Research vol. 24. No. 24 (1996) 4933-4939.
Bloom, et al, Applications of Numbered Undirected Graphs, Proceedings of the IEEE, vol. 65, No. 4, Apr. 1977, pp. 562-570.
Bourdoncle, A., et al., "Quaruplex-Based Molecular Beacons as Tunable DNA Probes", J. Am. Chem. Soc., vol. 128, No. 34, pp. 11094-11105, 2006.
Branton, Daniel et al, "The potential and challenges of anopore sequencing," Nature Biotechnology, vol. 26, No. 10, Oct. 2008, pp. 1146-1153.
Broude et al. (1994) Enhanced DNA sequencing by hybridization, Proc. Natl. Acad. Sci. USA, 91, 3072-3076.
Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.
Buchmueller, K.L., et. al., (2006) "Physical and Structural Basis for the Strong Interactions of the—ImPy—Central Pairing Motif in the Polyamide f-ImPylm," Biochemistry 45:13551-13565.
Cao, H., et al., (2002) "Fabrication of 10 nm Enclosed Nanofluidic Channels," Applied Physics Letters 81(1): 174-176.
Cao, H., et al., (2002) "Gradient Nanostructures for Interfacing Microfluidics and Nanofluidics," Applied Physics Letters 81:3058-3060.
Chen, C., et al., (1994) "Analogous Organic Synthesis of Small-Compound Libraries: Validation of Combinatorial Chemistry in Small-Molecule Synthesis," J. Am. Chem. Soc. 116:2661-2662.
Chen, P., et al., (2004) "Probing Single DNA Molecule Transport Using Fabricated Nanopores," Nano Letters 4:2293-2298.
Chetverin, A., et al., (1994) "Oligonucleotide Arrays: New Concepts and Possibilities," Bio/Technology 12:1093-1099.
Cox, M. (2007) "Motoring Along with the Bacterial RecA Protein," Nature Reviews—Molecular Cell Biology 9:127-138.
Decision to Grant dated Aug. 21, 2014 in European Patent Application No. 10 717 908.7-1559.
Dervan, P.B. (2001) "Molecular Recognition of DNA by Small Molecules," Bioorg. Med. Chem. 9:2215-2235.
Dervan, P.B., et al., (2003) "Recognition of the DNA minor groove by pyrrole-imidazole polyamides," Curr. Op. Struc. Biol. 13:284-299.
Doss, R.M., et al., (2006) "Programmable Oligomers for Minor Groove DNA Recognition," J. Am. Chem. Soc. 128:9074-9079.
Drmanac, R., et al. (1989) "Sequencing of Megabase Plus DNA by Hybridization: Theory of the Method," Genomics 4:114-128.
Drmanac, R., et al. (2002) "Sequencing by Hybridization (SBH): Advantages, Achievements, and Opportunities," Advances in Biochemical Engineering/Biotechnology, vol. 77: 75-101.
Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.
Examination Report dated Feb. 7, 2013 in European Application No. 10 717 908.7-1240 (4 pages).
Examination Report dated Jun. 11, 2014 in European Patent Application No. 11 785 507.2-1404, 8 pages.
Examination Report dated Jun. 3, 2014 in European Patent Application No. 08 835 216.6, 5 pages.
Examination Report dated Mar. 4, 2013 in European Application No. 08 835 216.6-1404 (6 pages).
Examination Report dated Oct. 23, 2014 in European Patent Application No. 11 785 257.4-1404, 6 pages.
Examination Report dated Oct. 29, 2014 in European Patent Application No. 09 748 871.2-1408, 5 pages.
Farkas, Z., et al., (2003) "DNA Uptake Into Nuclei: Numerical and Analytical Results," J. Phys.: Condens. Matter 15:S1767-S1777.
Fechter, E.J., et al., (2005) "Sequence-specific Fluorescence Detection of DNA by Polyamide-Thiazole Orange Conjugates," J. Am. Chem. Soc. 127:16685-16691.
Floreancig, P.E., et al., (2000) "Recognition of the Minor Groove of DNA by Hairpin Polyamides Containing $\alpha$-Substituted-,$\beta$-Amino Acids," J. Am. Chem. Soc. 122:6342-6350.
Fodor, S., et al., (2005) "Light-Directed, Spatially Addressable Parall Chemical Synthesis" Research Article 6 pgs.
Fologea, D., et al., (2005) "Slowing DNA Translocation in a Solid-State Nanopore," *Nano Lett.* 5(9):1734-7.
Frieze, A., et al., (1999) "Optimal Reconstruction of a Sequence From its Probes," 12 pgs.
Gerland, U., et al., (2004) "Translocation of Structured Polynucleotides Through Nanopores," Phys. Biol. 1:19-26.
Gershow, M., et al., (2007) "Recapturing and Trapping Single Molecules with a Solid-State Nanopore," Nature Nanotech. 2:775-779.
Ghosh, et al, Detection of Double-Stranded DNA: molecular methods and applications for DNA diagnostics Molecular Biosystems (2006) vol. 2, pp. 551-560.
Giehart B., et al., (2008) "Nanopore with transverse nanoelectrodes for electrical characterization and sequencing of DNA" Sensors and Actuators B., Elsevier Sequoia S.A, ScienceDirect,132:2 pp. 593-600.
Gracheva, M., et al., (2002) "Simulation of the Electric Response of DNA Translocation through a Semiconductor Nanopore-Capacitor," Nanotechnology 17:622-633.
Greer, E. et al., "Histone methylation: a dynamic mark in health, disease and inheritance," Nature Review: Genetics, May 2012, pp. 343-357, vol. 13, Macmillan Publishers Limited.
Guo, L. (2004) "Recent Progress in Nanoimprint Technology and its Application," J. Phys. D: Appl. Phys 37:R123-R141 (Appendices B-D).
Gygi, M.P., et al., (2002) "Use of fluorescent sequence-specific polyamides to discriminate human chromosomes by microscopy and flow cytometry," Nucleic Acids Research 30:2790-2799.
Halby, L., et al., (2005) "Functionalized head-to-head hairpin polyamides: Synthesis, double-stranded DNA-binding activity and affinity," Bioorg. Med. Chem. Lett. 15:3720-3724.
Hannenhalli S. et al. Comput Appl Biosci (1996) 12 (1): 19-24.
Heller, C., (2001) "Principles of DNA Separation with Capillary Electrophoresis," Electrophoresis 22:629-643.
Heng, J., et al., (2004) "Sizing DNA Using a Nanometer-Diameter Pore," Biophysical Journal 87:2905-2911.
Heyn, H. et al., "DNA methylation profiling in the clinic: applications and challenges," Nature Review: Genetics, Oct. 2012, pp. 679-692, vol. 13, Macmillan Publishers Limited.
Hudson, B., (1999) "An Experimental Study of SBH with Gapped Probes," 50 pgs.
Intention to Grant dated Jun. 26, 2014 in European Patent Application No. 10 717 908.7-1559.
Intention to Grant dated Mar. 25, 2014 in European Patent Application No. 10 717 908.7-1559.
International Preliminary Report on Patentability in PCT/US2012/024708 dated Aug. 13, 2013.
International Preliminary Report on Patentability issuance dated Apr. 7, 2010, PCT/US2008/078432.
International Preliminary Report on Patentability, Application No. PCT/US2010/028848, issuance dated Sep. 27, 2011, 8 pages.
International Preliminary Report on Patentability, Application No. PCT/US2009/055878, dated Nov. 29, 2011, 9 pages.
International Preliminary Report on Patentability, Application No. PCT/US2011/053274, issuance dated May 28, 2013, 14 pages.
International Preliminary Report on Patentability, Application No. PCT/US2011/059933, issuance dated May 21, 2013, 8 pages.
International Preliminary Report on Patentability, issuance of report dated Mar. 8, 2011, Application No. PCT/US2009/055876.
International Search Report and Written Opinion dated Feb. 10, 2010, PCT/US09/558876, 5 pages.

(56) References Cited

OTHER PUBLICATIONS

International Search Report and Written Opinion dated Feb. 5, 2009, PCT/US08/078432.
International Search Report and Written Opinion dated Jul. 29, 2014, PCT/US13/061651, 16 pages.
International Search Report and Written Opinion dated Jul. 29, 2014, PCT/US14/021756, 11 pages.
International Search Report and Written Opinion dated Jun. 26, 2014, PCT/US14/011829, 16 pages.
International Search Report and Written Opinion dated Jun. 29, 2010, PCT/US09/055876, 15 pages.
International Search Report and Written Opinion dated Mar. 24, 2010, PCT/US09/055878, 14 pages.
International Search Report and Written Opinion dated Oct. 25, 2012, PCT/US12/024708.
International Search Report and Written Opinion dated Sep. 30, 2010, PCT/US2010/028848, 14 pages.
International Search Report and Written Opinion, PCT/US2011/053274, dated May 2, 2013.
International Search Report and Written Opinion, PCT/US2011/059933, dated Apr. 2, 2012.
International Search Report for PCT/US04/04138, dated May 4, 2006, 5 pages.
Invitation to Pay Additional Fees and, Where Applicable, Protest Fee & Partial International Search dated Feb. 15, 2013, PCT/US2011/053274, 9 pages.
Invitation to Pay Additional Fees and, Where Applicable, Protest Fee & Partial International Search dated Jul. 10, 2012, PCT/US2012/024708, 10 pages.
Invitation to Pay Additional Fees and, Where Applicable, Protest Fee & Partial International Search dated Mar. 3, 2014, PCT/US2013/061651, 5 pages.
Jonsson, U., et al., (1991) "Real-Time Biospecific Interaction Analysis Using Surface Plasmon Resonance and a Sensor Chip Technology," BioTechniques, 11:620-627.
Ju et al., "Four-color DNA Sequencing by Synthesis Using Cleavable Fluorescent Nucleotide Reversible Terminators," Proc. Nat. Acad. Sci. USA (2006) 103:19635-19640.
Kalaugher, L., (2002) "Diffraction Gradient Lithography Aids Nanofluidics," Nanotechweb.org.
Kanehisa, L. (1984) "Use of Statistical Criteria for Screening Potential Homologies in Nucleic Acid Sequences," Nucleic Acids Research 12:203-213.
Kasianowicz et al., "Characterization of Individual Polynucleotide Molecules Using a Membrane Channel," Proc. Nat. Acad. Sci. USA 93:13770-13773 (1996).
Khrapko, K.R., et al., (1989) "An Oligonucleotide Hybridization Approach to DNA Sequencing," FEBS Lett. 256:118-22.
Kim, C., et al., (1992) "Binding Properties of Replication Protein A from Human and Yeast Cells," Mol. and Cell. Bio. 12(7):3050-3059.
Koike, Shinji et al., "Investigation into the Degrading Mechanism of Positive Electrodes after Calendar Life Test Using Transmission Electron Microscopy", 214th ECS Meeting, Abstract #569, The Electrochemical Society, Osaka, Japan, 1 page, 2008.
Kuo, et al., "Hybrid three-dimensional nanofluidic/microfluidic devices using; molecular gates," Sensors and Actuators A, vol. 102 (Oct. 2002):223-233.
Langa, "Self-organized growth of single crystals of nanopores," Applied Physics Letters, AIP, American Institute of Physics, 2003, vol. 82, No. 2, pp. 278-280.
Langer-Safer, P. et al., "Immunological method for mapping genes on *Drosophila* polytene chromosomes," Proc. Natl. Acad. Sci. USA, Jul. 1982, pp. 4381-4385, vol. 79.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Li et al., "Ion-beam sculpting at nanometre length scales", Nature 412,166-169 (2001).
Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.
Liang, X., et al., (2008) "Nanogap Detector Inside Nanofluidic Channel for Fast Real Time Label-Free DNA Analysis," Nano Letters 8:1472-76.
Ling, X., et al., "Hybridization Assisted Nanopore Sequencing," Patent Specification, 32 pgs.
Loakes, D., et al., (1994) "5-Nitroindole as an Universal Base Analogue," Nucleic Acids Research 22:4039-4043.
Loakes, D., et al., (1995) "3-Nitropyrrole and 5-Nitroindole as Universal Bases in Primers for DNA Sequencing and PCR," 23:2361-2366.
Lohman, T., et al., (1994) "*Escherichia coli* Single-Stranded DNA-Binding Protein: Multiple DNA-Binding Modes and Cooperatives," Annu. Rev. Biochem. 63:527-70.
Losi, et al., "Time-Resolved Absorption and Photothermal Measurements with Recombinant; Sensory Rhodopsin II from Natronobacterium pharaonis," Biophys. J. 77, 3277-3286,; Dec. 1999.
Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].
Marguiles et al., (2005) "Genome Sequencing in Microfabricated High-Density Picolitre Reactors," Nature 437:376-380.
Marques, M.A., et al., (2004) "Expanding the Repertoire of Heterocycle Ring Pairs for Programmable Minor Groove DNA Recognition," J. Am. Chem. Soc. 126:10339-10349.
McEntee, K., et al. "Binding of the RecA Protein of *Escherichia coli* to Single- and Double-Stranded DNA." J. Biol. Chem. (1981) 256:8835.
Meller, A., et al., (2000) "Rapid Nanopore Discrimination Between Single Polynucleotide Molecules," PNAS 97:1079-1084.
Meller, et al., "Voltage-driven DNA translocations through a nanopore," Phys. Rev. Lett.; 86(15),3435-3438 (2001).
Nice, E., et al., (1993) "Mapping of the Antibody- and Receptor-Binding Domains of Granulocyte Colony-Stimulating Factor Using an Optical Biosensor," Journal of Chromatography 646:159-168.
Nichols, R., et al., (1994) "A Universal Nucleoside for Use at Ambiguous Sites in DNA Primers," Letters to Nature, 369:492-493.
Notice of Final Rejection dated Jul. 2, 2014 in Japanese Patent Application No. 2011-525300.
Notice of Reasons for Rejection dated Jun. 17, 2013 in Japanese Patent Application No. 2011-525300.
Notification of the First Office Action dated Sep. 28, 2012 in Chinese Patent Application No. 200980140663.0.
Notification of the Second Office Action dated Apr. 2, 2013 in Chinese Patent Application No. 200980140663.0.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.
Olasagasti, F.; Lieberman, K. R.; Benner, S.; Cherf, G. M.; Dahl, J. M.; Deamer, D. W.; Akeson, M. *Nat. Nanotechnol.* 2010, 5, 798-806.
Optical Tweezers: Introduction to Optical Tweezers, Retrieved Sep. 29, 2003 from; http://www.nbi.dk/-tweezer/introduction.htm, pp. 1-5.
Pablo, P.J., et al., (2000) "Absence of dc-Conductivity." Phys. Rev. Lett. 85:4992-4995.
Park, P., "ChIP-seq: advantages and challenges of a maturing technology," Nature Reviews: Genetics, Oct. 2009, pp. 669-680, vol. 10, Macmillan Publishers Limited.
Pastor, W. et al., "Genome-wide mapping of 5-hydroxymethylcytosine in embryonic stem cells," Nature, May 19, 2011, pp. 394-397, vol. 473, Macmillan Publishers Limited.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P. et al., (1991) "Improved Chips for Sequencing by Hybridization," Journal of Biomolecular Structure & Dynamics 9:399-410.

(56) References Cited

OTHER PUBLICATIONS

Pevzner, P., (1989) "1-Tuple DNA Sequencing: Computer Analysis," Journal of Biomolecular Structure & Dynamics 7:63-73.
Powell, M., et al., (1993) "Characterization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et. al., (2000) "Sequencing-by-Hybridization at the Information-Theory Bound: An Optimal Algorithm," J. Comp. Biol. 7: 621-630.
Quake et al., (2003) "Sequence information can be obtained from single DNA molecules," Proc. Nat. Acad. Sci. USA 100:3960-3964.
Rapley, Ralph, "Direct Sequencing of PCR Products with DNA-Binding Proteins", Methods in Molecular Biology, vol. 65, Humana Press Inc., Totowa, NJ, pp. 101-104.
Rapley, Ralph, "Enhancing PCR Amplification and Sequencing Using DNA-Binding Proteins", Molecular Biotechnology, vol. 2, pp. 295-298, 1994.
Rehrauer, William M. et al., "Alteration of the Nucleoisude Triphosphate (NTP) Catalytic Domain within *Escherichia coli* recA Protein Attenuates NTP Hydrolysis but Not Joint Molecule Formation"pp. 1292-1297, The Journal of Biological Chemistry, The American Society for Biochemistry and Molecule Biology, Inc., vol. 268, No. 2, Jan. 15, 1993.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Riehn, R. et al., "Restricting Mapping in Nanofluidic Devices," Proceedings of the National Academy of Sciences of the United States of America, (2005) 102:1012-10016.
Robertson, J., et al., (2007) "Single-Molecule Mass Spectrometry in Solution Using a Solitary Nanopore," PNAS 104:8207-8211.
Ross-Innes, C. et al., "Differential oestrogen receptor binding is associated with clinical outcome in breast cancer," Nature, Jan. 2012, pp. 389-394, vol. 481, Macmillan Publishers Limited.
Rucker, V.C., et al., (2003) "Sequence Specific Fluorescence Detection of Double Strand DNA," J. Am. Chem. Soc. 125:1195-1202.
Salpea, P. et al., "Postnatal development- and age-related changes in DNA-methylation patterns in the human genome," Nucleic Acids Research, 2012, pp. 6477-6494, vol. 40, No. 14, Oxford University Press.
Sanger, F. et al., (1977) "DNA Sequencing with Chain-Terminating Inhibitors," Proc. Natl. Acad. Sci. USA 12:5463-5467.
Shim et al., "Detection and Quantification of Methylation in DNA using Solid-State Nanopores", Scientific Reports, www.nature.com, Mar. 11, 2013, pp. 1-8.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Shoaib, M. et al., "PUB-NChIP—"in vivo biotinylation" approach to study chromatin in proximity to a protein of interest," Genome Research, 2013, pp. 331-340, vol. 23, Cold Spring Harbor Laboratory Press, www.genome.org.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Stephen et al., "DNA manipulation sorting, and mapping in nanofluidic systems," Chemical Society Reviews, vol. 39, No. 3, Jan. 1, 2010, p. 1133.
Storm, A., et al., (2005) "Fast DNA Translocation through a Solid-State Nanopore," Nano Letters 5(7):1193-1197.
Storm, et al., "Fabrication of solid-state nanopores with single-nanometre precision," Nature; Materials 2,537-540, Aug. 2003.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, "Less is more," Nature 412, 135-136, Jul. 2001.
Terwilliger, T., et al., (1996) "Gene V Protein Dimerization and Cooperativity of Binding to Poly (dA)," Biochemistry 35:16652-16664.
Thompson et al., "Detection of Structural Variations Using Nanodetector Positional Sequencing," AGBT Meeting, Feb. 1, 2012.
Thompson et al., "Mapping and sequencing DNA using nanopores and nanodetectors," Electrophoresis, vol. 33, No. 23, Dec. 12, 2012, pp. 3429-3436.
Thompson et al., "Structural Variations Identified Using Solid-State Nanodetectors," Meeting of the American Society for Human Genetics, Nov. 9, 2012.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Van Steensel, B. et al., "Identification of in vivo DNA targets of chromatin proteins using tethered Dam methyltransferase," Nature Biotechnology, Apr. 2000, pp. 424-428, vol. 18.
Venkatesan et al., "Stacked Graphene-Al2O3 Nanopore Sensors for Sensitive Detection of DNA and DNA-Protein Complexes", www.acsnano.org, vol. 6, No. 1, 2012, pp. 441-450.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Waugh, David S., "Make the most of affinity tags", pp. 316-320, Trends in Biotechnology, Science Direct, vol. 23, No. 6, Jun. 2005.
Web article (2003) "DNA Combed Into Nanochannels," http://www.nature.com.
Written Opinion dated Jul. 1, 2008, PCT/US06/38748, 6 pages.
Wu et al., "On-column conductivity detection in capillary-chip electrophoresis", 2007, 28, 4612-4619.
Zhang, W., et al., (2006) "Discrimination of Hairpin Polyamides with an α-Substituted-γ-aminobutyric Acid as a 5'-TG-3' Reader in DNA Minor Groove," J. Am. Chem. Soc. 128:8766-8776.
Zwolak, M., et al., (2008) "Colloquium: Physical Approaches to DNA Sequencing and Detection." Rev. Mod. Phy. 80:141-165 (J).
Partial International Search Report dated Feb. 15, 2010, PCT/US09/055878, 3 pages.
Invitation to Pay Additional Fees and, Where Applicable, Protest Fee & Partial International Search dated Aug. 19, 2010, PCT/US2010/028848, 7 pages.
International Preliminary Report on Patentability dated Apr. 9, 2015 in PCT/US2013/061651, 10 pages.
International Preliminary Report on Patentability dated Sep. 24, 2015 in PCT/US2014/021756, 8 pages.
Vercoutere et al., "Rapid discrimination among individual DNA hairpin molecules at single-nucleotide resolution using an ion channel" nature biotechnology, vol. 19, Mar. 2001.
Howorka et al., "Sequence-specific detection of individual DNA strands using engineered nanopores", nature biotechnology, vol. 19, Jul. 2001.
Viruses (Wikipedia.com, accessed Nov. 24, 2012).
How many species of bacteria are there (wisegeek.com; accessed Jan. 21, 2014).
Fungi, (Wikipedia.com; accessed Jun. 3, 2013).
Plant, (Wikipedia.com; accessed Mar. 8, 2013).
Mammal, (Wikipedia.com; accessed Sep. 22, 2011 ).
Murinae, (Wikipedia.com; accessed Mar. 18, 2013).
Fish, (Wikipedia.com, accessed Nov. 2, 2014).
List of sequenced bacterial genomes (Wikipedia.com; accessed Jan. 24, 2014).
Intention to Grant dated Oct. 20, 2015 in European Patent Application No. 11 785 257.4-1404.

(56) References Cited

OTHER PUBLICATIONS

Notice of Reasons for Rejection in Japanese Patent Application No. 2013-538841 dated Nov. 12, 2015 9 pages.
Examination Report in European Patent Application No. EP 09 807 476.8-1554 dated Apr. 1, 2015 6 pages.
Examination Report in European Patent Application No. EP 09 748 871.2-1408 dated Sep. 9, 2015 4 pages.
Notification of Reexamination in Chinese Patent Application No. 200980140663.0 dated Nov. 25, 2015 15 pages.
Final Office Action in Japanese Patent Application No. 2014-218935 dated Jan. 4, 2016 one page.
Notice of Allowance in Japanese Patent Application No. 2013-538841 dated Jul. 7, 2016 3 pages.
Office Action in Japanese Patent Application No. 2014-218935 dated Jul. 27, 2015 3 pages.
Notice of Reasons for Rejection in Japanese Patent Application No. 2013-530398 dated Sep. 14, 2015.
Office Action in European Patent Application No. 08 835 216.6 dated Mar. 24, 2016 1 page.
Decision to Grant dated Mar. 10, 2016 in European Patent Application No. 11785257.4.
Examination Report dated Apr. 25, 2016 in European Patent Application No. 13 792 116.9-1408 6 pages.
"About Lock-In Amplifiers" (Stanford Research), last modified Jan. 19, 2004 and accessed Mar. 29, 2016 at http://www.thinksrs.com/downloads/PDFs/ApplicationNotes/AboutLIAS.pdf.
Bai, et al., "Passive Conductivity Detection for Capillary Electrophoresis," Analytical Chemistry, vol. 76, 2004, pp. 3126-3131.
Laugere, et al., "On-Chip Contactless Four-Electrode Conductivity Detection for Capillary Electrophoresis Devices," Analytical Chemistry, vol. 75, pp. 306-312, Jan. 2003.
Communication Pursued to Article 94(3) EPC dated on Aug. 30, 2016 in European Patent Application No. 14 706 709.4, 3 pages.
Notice of Reasons for Rejection in Japanese Patent Application No. 2013-530398 dated Aug. 25, 2016.
International Preliminary Report and Written Opinion dated Sep. 15, 2015, PCT/US2014/021756, 8 pages.
International Preliminary Report and Written Opinion dated Feb. 8, 2016, PCT/US2015/049765, 19 pages.
International Preliminary Report and Written Opinion dated Mar. 23, 2017, PCT/US2015/049765, 13 pages.

* cited by examiner

APPARATUS AND METHODS FOR ANALYSIS OF BIOMOLECULES USING HIGH FREQUENCY ALTERNATING CURRENT EXCITATION

RELATED APPLICATION

This application claims the benefit of priority under 35 U.S.C. § 119(e) to U.S. Provisional Patent Application Ser. No. 61/740,146 filed Dec. 20, 2012, the entirety of which is incorporated herein by reference.

FIELD OF INVENTION

The present invention relates generally to assay methods for the analysis of biopolymers. Mapping and sequencing of such biopolymers is contemplated herein.

BACKGROUND

A number of different approaches for sequencing nucleic acids exist. The traditional methods are the dideoxy-chain termination method described by Sanger et al., Proc Natl. Acad. Sci. USA, (1977) 74: 5463-67 and the chemical degradation method described by Maxam et al., Proc. Natl. Acad. Sci. USA, (1977) 74: 560-564. Of these two methods, the Sanger procedure has been the most widely used. The original Sanger method relied on radioactive labeling of the reaction products and separation of the reaction products by slab gel electrophoresis.

Both the Sanger and Maxam methods are time- and labor-intensive. The start of the Human Genome Project was the impetus for the development of improved, automated systems to perform Sanger sequencing. As a result, detection of fluorescence has replaced autoradiography and capillary electrophoresis has replaced the ultrathin slab gels originally used to separate reaction products. Automated sequencers have been developed and are capable of processing large numbers of samples without operator intervention.

The completion of the Human Genome Project has refocused the need for new technologies that are capable of rapidly and inexpensively determining the sequence of human and other genomes. There is has been much discussion in recent years about personalized medicine. The vision of personalized medicine involves every individual having his or her complete genome sequenced at high accuracy and using this information to guide clinical care, specifically for risk stratification of patients and pharmacogenomics.

In recent years, a number of technological advances have been developed enabling a great reduction in the cost of sequencing and substantially increasing the amount of sequence data produced. Most sequencing methods currently available utilize optical detection for the determination of the DNA sequence. The most prevalent sequencing methods are referred to as sequencing by synthesis (SBS).

Typical embodiments of SBS consist of the stepwise synthesis of a strand of DNA that is complementary to a template sequence from the target genome to be sequenced. The SBS methods can be divided into those that are performed in batch mode and those that are performed in real-time. The batch mode processes rely on the stepwise synthesis of the new DNA strand with the limitation that the synthesis is only allowed to proceed for one nucleotide position, for one nucleotide type, or for the combination of one nucleotide position and one nucleotide type. The incorporation of the nucleotide occurs in parallel for large numbers of templates. Detection is achieved using a variety of methods.

Embodiments of the batch mode utilizing a single nucleotide type are used by Roche for pyrosequencing with the 454 platform. The Roche technology (see, e.g., Margulies et al. (2005) Nature, 437:376-380; U.S. Pat. Nos. 6,274,320; 6,258,568; 6,210,891) utilizes pyrosequencing. The method depends on several enzymes and cofactors to produce luminescence when a nucleotide is incorporated. A single nucleotide species is introduced into a large number of small reaction vessels each containing multiple copies of a single template. The incorporation of the nucleotide is accompanied by light emission. When the reaction has run to completion, the reagents are washed from the reaction volumes and a next nucleotide and its required reagents are washed into the reactions. Each template is thus extended in an iterative fashion, one nucleotide at a time. Multiple incorporations of the same nucleotide require the quantitative determination of the amount of light emitted. Homopolymer tracts in templates may be difficult to accurately sequence as the incremental amount of light emitted for each subsequent position in the homopolymer becomes small compared to the total amount emitted.

In a second embodiment of the SBS method, platforms by Helicos (see, e.g., Quake et al Proc. Nat. Acad. Sci. USA (2003) 100: 3960-3964; U.S. Pat. Nos. 6,818,395; 6,911, 345; 7,297,518; 7,462,449 and 7,501,245), Illumina (see, e.g., Bennett et al. Pharmacogenomics (2005) 6:373-382), and Intelligent Bio-Systems (see, e.g., Ju et al. Proc. Nat. Acad. Sci. USA (2006) 103:19635-19640) allow only the incorporation of a single nucleotide at each step. Template strands are attached to a solid support and a primer sequence is annealed. A polymerase is used to extend the primer to make a complement to the template. The nucleotides are derivatized such that after the incorporation of a single nucleotide, the growing strand is incapable of further extension. The nucleotides are further derivatized to make them fluorescent. In the Helicos technology, the four nucleotides are labeled with the same fluorescent tag. This requires that each nucleotide type be added separately. In contrast, the Illumina and Intelligent Bio-Systems technologies utilize four different fluorescent tags so that a mixture of all four derivatized nucleotides may be added at the same time. For both technologies, the incorporation of a nucleotide is accompanied by the appearance of fluorescence in the growing strand. In the case of Illumina, the wavelength of the fluorescence emission indicates the identity of the newly incorporated nucleotide. In the Helicos technology, only a single nucleotide type is added at each cycle. Thus, the appearance of fluorescence at a position on the solid support indicates the incorporation of the added nucleotide for that template. Templates that do not incorporate the nucleotide present in the reaction remain dark.

Following the observation of any incorporated fluorescence, the blocking groups and fluorescent tags are removed prior to the next cycle. Multiple cycles result in the acquisition of sequence data for many templates in a single run. The instrumentation typical for these technologies is said to allow for the automated acquisition of sequence information for hundreds of thousands to millions of templates in parallel.

SBS methods may also be performed in real-time. In this embodiment, polymerase is used to incorporate fluorescently labeled nucleotides and the fluorescence is observed during DNA strand synthesis. The four nucleotides are labeled with different fluorescent tags. The fluorescent tags are attached to the terminal phosphate of the nucleotide triphosphate. During incorporation of the nucleotide into the growing strand the fluorophore is released to solution and the growing strand remains non-fluorescent. The identity of the incorporated strand is determined while the nucleotide resides in the active site of the enzyme and before the cleaved diphosphate is released to bulk solution.

The fluorescence of the incorporated nucleotide typically is measured in a background fluorescence from a much larger concentration of unincorporated nucleotide. Pacific Biosciences (see, e.g., U.S. Pat. Nos. 7,170,050; 7,302,146; 7,315,019; 7,476,503; and 7,476,504) identifies the incorporated nucleotide based on the residence time in the polymerase active site. Fluorescence emission from the active site for an appropriate time indicates incorporation and the emission wavelength determines the identity of the incorporated nucleotide. Polymerase is attached to the bottom of zero-mode waveguides. Zero-mode waveguides are reaction cells whose dimensions limit the passage of light from the excitation sources. Thus, only fluorescent tags close to the bottom surface of the reaction volume are excited.

Visigen identifies the incorporated nucleotide through Fluorescent Resonant Energy Transfer (FRET) between an acceptor in the polymerase active site and a fluorescent tag on the nucleotide (see, e.g., U.S. Pat. Nos. 7,211,414 and 7,329,492). Only nucleotides held in the active site of the polymerase show fluorescence. Incorporation is identified by the residence time of the fluorescence in the active site and the nucleotide identity is determined by the emission wavelength.

Other recently developed methods to sequence DNA rely on hybridization and ligation. Both the SOLiD and Complete Genomics technologies rely on the combination of hybridization and ligation. The SOLiD system (Life Technologies) immobilizes short template strands via an adapter. A primer and a pool of labeled oligonucleotides containing two fixed positions and six degenerate positions is hybridized to the template. The primer hybridizes to the adaptor. Each pool consists of 16,384 different sequences. Four fluorescent dyes are used to label the oligonucleotides in a pool in a fashion that creates four subsets from the sixteen combinations at the two fixed positions. Thus, each fluorescent tag is associated with four of the sixteen possible combinations. Following hybridization, a ligase is added and any probes in the pool that hybridized contiguously with the primer are ligated to the primer. The fluorescence of the hybridized and ligated product is determined. The fluorescence defines which subset of sequences hybridized to the template and ligated to the primer. The terminal three bases and the associated fluorescent tag are cleaved from the hybridized and ligated oligonucleotide. Subsequent rounds of another round of hybridization, ligation, and cleavage are performed. In this first series of reactions, each cycle identifies a subset for the pair of nucleotides in the template that is 5 nucleotides downstream from subset of pairs that were identified in the last cycle. After several cycles, the primer, and the oligonucleotides that have been ligated to it, is washed off the template The entire procedure is repeated starting with a primer that is one nucleotide shorter than the original primer, then with primers that are two, three, and four nucleotides shorter than the original primer. These subsequent rounds shift the frame of interrogation so that the bases that make-up the template strand can be identified from the union between the two subsets of reaction that overlapped at that position.

Complete Genomics technology utilizes a similar hybridization and ligation method (see, e.g., US Patent Application Publication Nos. 20080234136; 20090005252; 20090011943; and 20090176652). In the Complete Genomics technology, a primer is hybridized to an adaptor that is attached to the end of the template. A series of pools of oligonucleotides is constructed. In each pool, the nucleotide at a single position is identified by using four-color fluorescence. The remaining positions are degenerate. The first pool is hybridized to the template. Oligonucleotides that hybridize adjacent to the primer are subsequently ligated. After washing excess oligonucleotides away, the fluorescence of the ligated oligonucleotide identifies the nucleotide at the defined position in that pool. The ligated primer and oligonucleotide are washed off the template and the process is repeated with the next pool of oligonucleotides that probe the next position down from the primer.

The SBS and hybridization-ligation methods generate short pieces or reads of DNA sequence. While the short reads can be used to re-sequence human genomes, they are not favorable for the de novo assembly of human genomes. With the recent realization that human genomes contain large numbers of inversions, translocations, duplications, and indels (e.g., mutations that include both insertions, deletions, and the combination thereof), the quality of human genome data from short reads is even more suspect. Genetic rearrangements are even more prevalent in cancer.

While embodiments of the short read technologies that incorporate paired-end reads have been proposed and the length of the sequence data from these technologies has increased incrementally over the last two years, it is clear that longer read technologies are necessary for the accurate assembly of human genome data.

In addition to the undesirable nature of short reads, all of the DNA sequencing methods described above employ optical detection. The throughput of optical methods limits the ultimate performance characteristics of any of these sequencing technologies. Optical methods are capable of identifying single molecules. However, the time required to observe and accurately identify events is typically too slow to meet the need for higher throughput. While the current generation of sequencing technologies has lowered the cost of sequencing by orders of magnitude in comparison to the methods used to sequence the first human genomes, the methods remain too slow, costly, and inaccurate for routine analysis of human genomes.

A need therefore exists for efficient methods and devices capable of rapid and accurate nucleic acid sequencing for de novo assembly of human genomes. It is desirable to have long read lengths and to use as little nucleic acid template as possible. Moreover, single-molecule optical detection of DNA has limitations with respect to sensitivity and speed.

Thus, there remains a need for improved methods and devices for the analysis of biopolymers, including methods and devices for mapping and sequencing such biopolymers.

SUMMARY OF THE INVENTION

Embodiments of the invention relate to devices and methods for mapping and sequencing biomolecule analytes using nanopores, nano-channels and micro-channels. Some embodiments of the invention feature the analysis of an alternating current (AC) excitation-induced potential across a detection volume. Systems using electrical detection of biomolecule analytes in nanopores, nano-channels and micro-channels have been described in the past. See, for example, US Patent Publication No. US2007/0190542 A1, and U.S. Pat. No. 8,246,799 the teachings of which are incorporated herein in their entirety. In these systems, electrical potential changes are probed via detector electrodes which define a detection volume in the channel or pore. The inventors have discovered that the application of an AC excitation signal across a detection volume makes it is possible to achieve significantly improved signal-to-noise ratio (SNR) performance, thereby facilitating the analysis.

In a broad embodiment, the invention relates to a device for analyzing a target biomolecule, having a substrate defining a fluidic channel or pore, and a mechanism for translocating a target biomolecule analyte through the fluidic channel or pore. The analyte may be a biomolecule having at least one region including a hybridized probe and at least one region lacking a hybridized probe. A plurality of detector electrodes are disposed in relation to the fluidic channel or pore, and these detector electrodes define at least one detection volume in the fluidic channel or pore. Circuitry is provided for supplying an AC voltage excitation signal to the detection volumes, and also for detecting a sensor signal associated with the detection volumes. The sensor signal is indicative of (i) the absence of the analyte in a detection volume, (ii) the presence of a portion of the analyte lacking a hybridized probe in the detection volume, and (iii) the presence of a portion of the analyte having a hybridized probe in the detection volume.

The device may be used in connection with a method for sequencing a target biomolecule, whereby a target biomolecule is hybridized with a probe set of a plurality of probes identical in sequence to provide a hybridized biomolecule analyte having probes hybridized to complementary regions thereon. Optionally the analyte is coated with one or more proteins. An apparatus having first and second fluid chambers in fluid communication with one another, and separated by a structure defining a micropore, a nanopore, a microchannel, and/or a nanochannel is provided. The apparatus further includes a plurality of detector electrodes defining detection volumes within the structure. An alternating current voltage excitation signal is applied across the detection volumes. The analyte is translocated through a detection volume, and an electrical property is monitored as a function of time, during the translocation. Variations in the monitored electrical property allow one to differentiate between hybridized and non-hybridized regions of the analyte based at least in part on detected changes in the electrical property in the detection volume. This information may be used to sequence at least a portion of the target biomolecule.

One or more of the following features may be included. The biomolecule may be, for example, a deoxyribonucleic acid, a ribonucleic acid, and/or a polypeptide. The structure may define at least one nanopore having a diameter of between about 1 nanometer and about 1 micrometer. The structure may define at least one microchannel having a width of between about 1 micrometer and about 25 micrometers. The structure may define at least one nanochannel having a width of between about 10 nanometers and about 1 micrometer. There may be more than one probe set used. The first probe set (and/or additional probe sets) may include hybridizing polyamides. The first probe set (and/or additional probe sets) may include oligomers of non-cognate bases. The first probe set (and/or additional probe sets) may include at least one of DNA, RNA, locked nucleic acids, and/or peptide nucleic acids. The first probe set (and/or additional probe sets) may include antibodies and/or fragments thereof.

The first probe set (and/or additional probe sets) may include hybridizing oligonucleotides having n number of contiguous bases capable of hybridizing to complementary regions on the biomolecule, where n is an integer, for example, from 4 to 12. The first probe set (and/or additional probe sets) may include gapped probes. The gapped probes may have 6 contiguous bases capable of hybridizing to complementary regions on the biomolecule. At least a portion of the probes in the first probe set (and/or additional probe sets) each may have attached thereto a detectable tag. The tag may not hybridize with the biomolecule. The optional coating step may include at least partially coating at least one of the partially hybridized biomolecule and the detectable tag with one or more proteins. The coating step may include at least partially coating the partially hybridized biomolecule and the detectable tag with one or more proteins. The one or more proteins in the coating step may include RecA, T4 gene 32 protein, f1 geneV protein, human replication protein A, Pf3 single-stranded binding protein, adenovirus DNA binding protein, and *E. coli* single-stranded binding protein. The tag may include a detectable identification region unique to its probe set, thereby allowing the specific probe set with which the tag is included to be identified. The tag may include a structured biomolecule, and the structured biomolecule may have a hairpin structure. The tag may include a detectable identification region that has a unique pattern of detectable loops formed in the structured biomolecule.

The description of elements of the embodiments above can be applied to this aspect of the invention as well.

BRIEF DESCRIPTION OF THE DRAWINGS

The objects and features of embodiments of the invention can be better understood with reference to the drawings described below, and the claims. The drawings are not necessarily to scale, emphasis instead generally being placed upon illustrating the principles of embodiments of the invention. In the drawings, like numerals are used to indicate like parts throughout the various views.

While embodiments of the invention are particularly shown and described herein with reference to specific examples and specific embodiments, it should be understood by those skilled in the art that various changes in form and detail may be made therein without departing from the spirit and scope of the invention.

DETAILED DESCRIPTION

Figure 1:
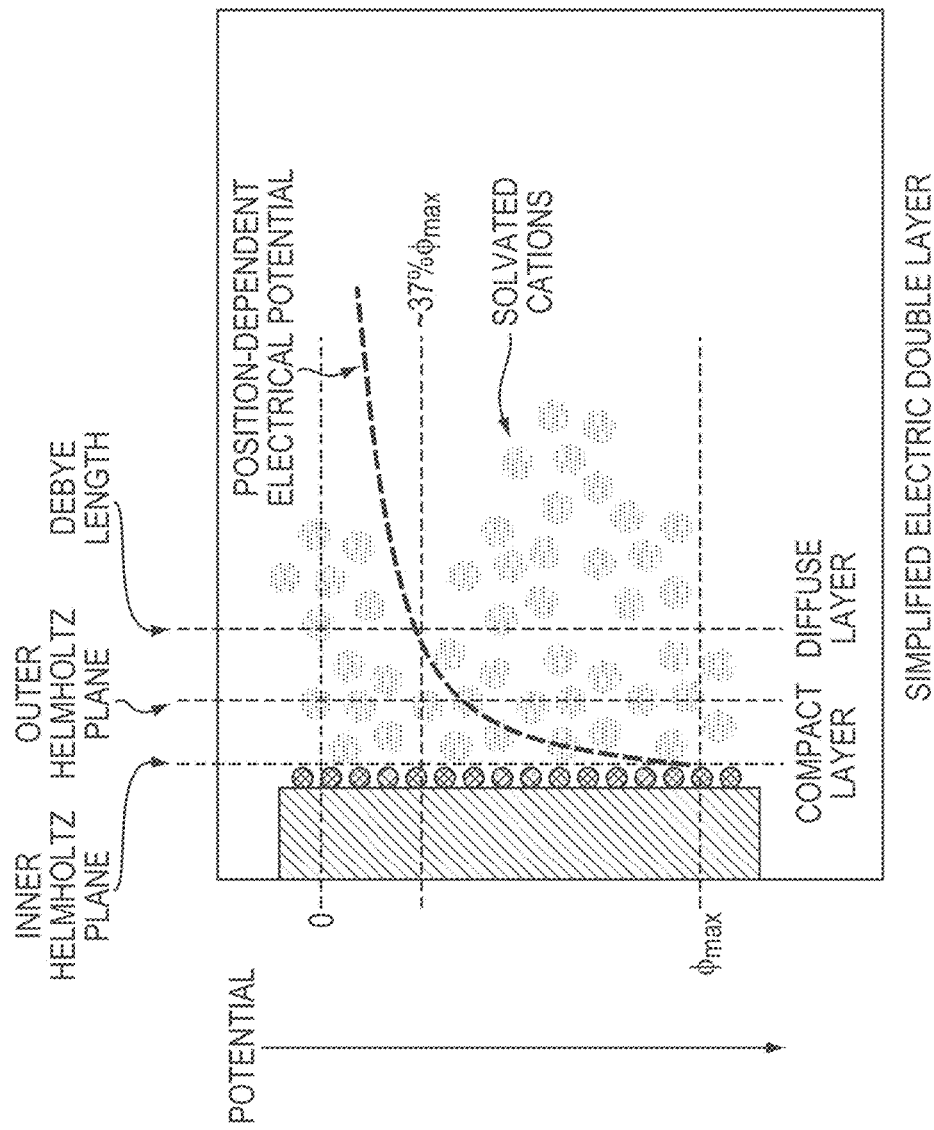
FIG. 1 is a schematic drawing depicting an electrical double layer that appears on the surface of an electrode in contact with fluid within fluidic channel or pore.

It is contemplated that embodiments of devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of embodiments the present invention that consist essentially of, or consist of, the recited components, and that there are embodiments of processes and methods according to the present invention that consist essentially of, or consist of, the recited processing steps.

It should be understood that the order of steps or order for performing certain actions is immaterial so long as embodiments of the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

All publications mentioned herein are incorporated herein in their entireties.

As used herein, the term "sequence" is not limited to an entire sequence but may include subsequences of a biomolecule, and the term "biomolecule" is not limited to an entire biomolecule but may include fragments of a biomolecule. The term "biomolecule" may include one or more copies of a given biomolecule (or fragment thereof), e.g., where a biomolecule is hybridized with one or more probes, this may mean hybridizing a large number of copies of a given biomolecule with many copies of the one or more probes.

As used herein, "target" means a biomolecule, for example, having sequence information that is to be determined using embodiments of the present invention. The target biomolecule may be a biopolymer such as a deoxyribonucleic acid, a ribonucleic acid, a protein, or a polypeptide. The target biomolecule may be single- or double-stranded.

As used herein, a "probe" means any molecule or assembly of molecules capable of sequence-specific binding to a target molecule, i.e., hybridization. A probe may be, but is not limited to, a DNA sequence, an RNA sequence, a locked nucleic acid (LNA) sequence, a peptide nucleic acid (PNA) sequence, antibodies or antibody fragments, and proteins. The terms "nucleotide" and "base" are used interchangeably and mean a molecule consisting of a phosphate group, a sugar and one of five nitrogen-containing bases that can make up DNA or RNA polynucleotide chains or strands. For DNA, the nitrogen-containing bases include cytosine (C), adenine (A), guanine (G) and thymine (T) and the sugar is a 2-deoxyribose. For RNA, the deoxyribose sugar is replaced by a ribose sugar instead of deoxyribose and uracil bases (U) instead of thymine bases (T). The probes may include oligomers of non-cognate bases. As used herein, "non-cognate" is intended to mean probes that bind to target sequences whose identity is not known. As noted above, in certain instances, further description of the embodiments of the present invention may refer to "DNA." Unless otherwise specified, such use is for simplification only, and it should be understood that such references are not intended to be limiting, and that references to DNA are intended to include all of the defined biopolymers described above, i.e., DNA, RNA, LNA, PNA, proteins, and polypeptides.

Embodiments of the present invention also envision the use of "gapped" probes, i.e., probes having a pattern of universal and designate nucleotides. A "universal" nucleotide, as used herein, is intended to mean a chemical entity which, when present in the probe, will engage in a base-pairing relationship with any natural nucleotide. Exemplary universal nucleotides include 5-nitroindole and 3-nitropyrrole. Further description of gapped probes may be found in U.S. Pat. Nos. 6,689,563; 7,034,143 & 7,071,324, the teachings of which are incorporated herein by reference.

The term "tag" means a moiety that is attached to a probe in order to make the probe more visible to a detector. These tags may be proteins, double-stranded DNA, single-stranded DNA or other molecules. In one preferred embodiment, such tags include DNA structures, such as hairpins, while in other embodiments, tags may include dendrimers, beads, or peptides. In certain embodiments, when used with nanopore detectors, tags may have either a larger volume than the probe or a different charge so that they slow translocation of the biomolecule through the nanopore or fluidic channel.

A DNA probe "library" is a collection of DNA probes of a fixed length that includes a large number of, or possibly all, possible sequence permutations of a given length. A plurality of probes may be made up of multiple copies of the same probe with the same sequence selectivity or be made up of two or more probes with different sequence selectivity.

A "probe map" means a data set containing information related to the sites along a target sequence at which a probe preferentially binds. The data set may include absolute positional information referenced to a known sequence, relative information related to distances between binding sites, or both.

A "partially hybridized biomolecule" is created when the entire length of a sequence-selective probe binds to a portion of the length of the target biomolecule.

A "detection volume" is the volume of electrolyte between two detector electrodes, through which an electrical property such as resistance or voltage is measured by the detector electrodes. The data set may be stored in computer media. Further details of the characteristics of probe and spectrum maps may be found in U.S. Patent Publication No. US2009/0099786 A1, which is incorporated herein by reference in its entirety.

In embodiments of the present invention, a DNA molecule or other biomolecule (i.e., the analyte) may be mapped or sequenced by hybridizing long fragments of an unknown target DNA with short probes of known sequence. These probes will selectively bind to the target DNA to create binding events wherever they find their complementary sequence. The distance between these binding events may be measured, for example, by sending the target fragments and hybridized probes through a detection volume present in a nanopore, nanochannel, micropore, or microchannel. As the analyte and attached probe travel through the detection volume, electrical properties such as current or voltage are measured across the detection volume thereby allowing the unlabeled or unhybridized backbone of the target DNA to be distinguished from hybridized regions on the backbone that include hybridized probes. A time course or time history of such measurements provides data which may be used to determine the distance between probe binding sites on the target DNA, thereby mapping the target. By repeating the method with a number of different probes, it is possible to sequence a portion of the DNA by aligning overlapping portions of the probe sequences.

Various microfluidic detection systems are described in published documents and may be used in various embodiments described herein, for example, U.S. Patent Application Publication No. US2007/0190542 A1, "Hybridization Assisted Nanopore Sequencing"; U.S. Pat. No. 8,278,047, "Biopolymer Sequencing by Hybridization of Probes to Form Ternary Complexes and Variable Range Alignment"; U.S. Patent Application Publication No. US2010/0096268 A1, "Use of Longitudinally Displaced Nanoscale Electrodes for Voltage Sensing of Biomolecules and Other Analytes in Fluidic Channels"; U.S. Patent Application Publication No. US2010/0243449 A1, "Devices and Methods for Analyzing Biomolecules and Probes Bound Thereto"; U.S. Patent Application Publication No. US2010/0261285 A1, "Tagged-Fragment Map Assembly"; U.S. Pat. No. 8,262,879, "Devices and Methods for Determining the Length of Biopolymers and Distances Between Probes Bound Thereto"; and U.S. Pat. No. 8,246,799, "Devices and Methods for Analyzing Biomolecules and Probes Bound Thereto," the texts of which are all incorporated herein by reference in their entirety. The methods, apparatus, and systems of the following pending patent applications may also be used in various embodiments described herein: U.S. Patent Publication Application No. 2012/0074925 "Assay Methods Using Nicking Endonucleases," by Oliver; and U.S. Patent Publication Application No. 2012/0122712, "Methods for Sequencing a Biomolecule by Detecting Relative Positions of Hybridized Probes," by Goldstein, the texts of which are all incorporated herein by reference in their entirety.

The methods and devices described herein are best described by first considering that an electrode/fluid interface behaves as an electrical double layer, i.e., a double layer capacitor; therefore, an electrode pair can be modeled as two capacitors in series with the detection volume between the electrode pair. FIG. 1 is a schematic drawing depicting an electrical double layer that appears on the surface of an electrode in contact with fluid within a detection volume. Two parallel layers of charge form on the surface of the electrode. The first layer is a surface charge composed of ions adsorbed directly onto the electrode, while the second layer is composed of ions attracted to the surface charge via the coulomb force, electrically screening the surface charge layer. Solvated cations are attracted to the negative surface charge, shielding the surface charge.

By applying AC voltage excitation directly across a detector electrode pair, current is driven through the double layer capacitances into the fluid. The net potential "seen" by the fluid within a detection volume is then the superposition of the AC voltage excitation-induced potential and the DC potential gradient applied via electromotive electrodes at either end of the pore or channel. The DC electric field that is applied to the channel or pore via the electromotive electrodes is substantially isolated from and independent of the excitation signal applied to the detection volume. Furthermore, the resistance of the detection volume varies depending on whether a portion of the analyte is present within the detection volume, as well as whether or not a probe is hybridized to the portion of the analyte that is present in the detection volume. Thus, by measuring voltage or current using the detector electrodes, it is possible to distinguish between three possible states of a given detection volume, as a function of time: (i) where there is no analyte in the detection volume; (ii) where there is a portion of the analyte lacking a hybridized probe in the detection volume; and (iii) where there is a portion of the analyte having a hybridized probe in the detection volume.

By applying AC voltage excitation directly across a detection volume, it is possible to achieve significantly improved signal-to-noise ratio performance, thereby improving the accuracy and workability of an analyte sequencing method that depends on distinguishing between these three possible states as a function of time.

Figure 2:
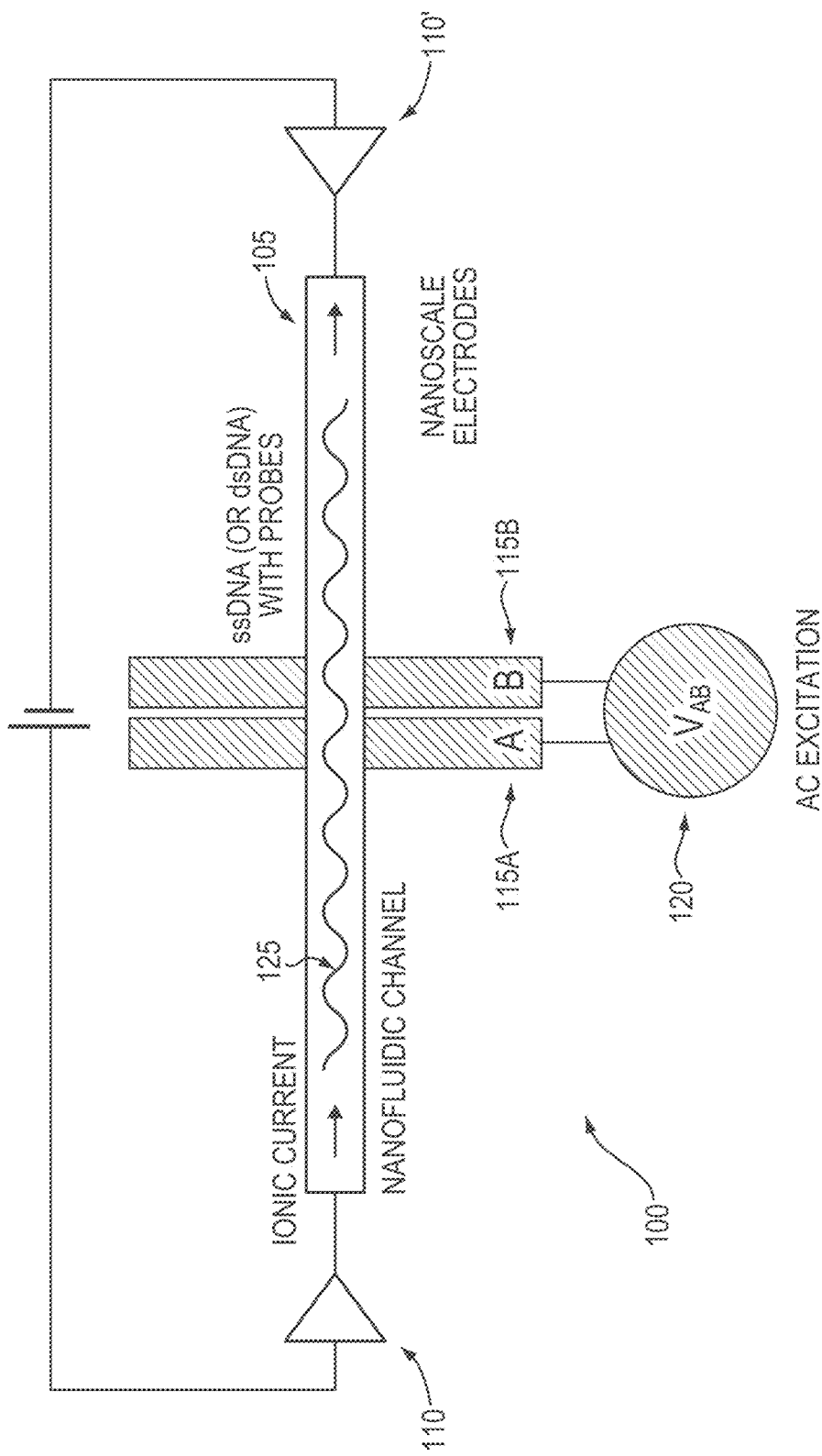
FIG. 2 is a schematic drawing of one illustrative embodiment of the invention, showing one pair of electromotive electrodes and one pair of detector electrodes defining a detection volume.

FIG. 2 shows a device (also referred to herein as a system or apparatus) 100 including a fluidic channel 105, (e.g., a micro- or nanochannel), a pair of electromotive electrodes 110, 110', and a pair of detector electrodes 115A, 115B, which define a detection volume. Importantly, a signal source 120 applies an AC voltage excitation signal across the detection volume in the nano-channel. The detector electrodes 115A, 115B are in electrical connection with the signal source 120. Circuitry associated with the detector electrodes is described in greater detail below.

The fluidic channel 105 may be defined in a substrate including silicon, silicon dioxide, fused silica, and/or gallium arsenide. The fluidic channel may contain an electrolytic solution, with electromotive electrodes 110, 110' being disposed, respectively, at first and second ends of the fluidic channel.

The electromotive electrode 110, 110' pair may include at least one anode 110' and cathode 110 in contact with the electrolytic solution to provide a constant or changing electrical current to drive the analyte 125 through the fluidic channel, thereby functioning as a driving force generator. In an alternate embodiment, the driving force generator may be a pressure differential that may be used to drive the analyte through the fluidic channel. Pressure may be supplied with a fluid pump or with a pressurized gas line. Other methods of applying a driving force for the analyte may be envisioned by one of skill in the art. In some embodiments, the driving force generator may include a chemical potential gradient that may be used to move molecules through the fluidic channel. Chemical potential gradients may be created with concentration gradients. For instance, a fluidic channel may have one end immersed in a fluid that has a higher salt concentration than the fluid at the other end of the fluidic channel. The differential in salt concentration at the ends of the fluidic channel may cause an osmotic pressure that can drive analytes through the fluidic channel. These methods may be used alone or in any combination.

As the analyte 125, which may be any biomolecule including, but not limited to, polypeptides, DNA or RNA, passes through the fluidic channel 105, it may pass between the pair of detector electrodes 115A, 115B (each individually referred to herein as "A" and "B").

The lateral distance along the channel, defined by the lateral offset between a pair of detector electrodes is referred to herein as the "detection volume". As will be described below, the apparatus is not limited to the use of one pair of detector electrodes; rather, systems with multiple detector electrodes, defining multiple detection volumes, are envisioned as well. The devices 100 described herein may be nanochannel devices formed by the fabrication of a fluidic channel 105 typically having nanoscale dimensions, and the fabrication of nanoscale electrodes. In some embodiments, the fluidic channel may have microscopic dimensions, e.g., may be a microchannel. A typical device may also have a microscale fluidic structure for introduction of buffers and samples. Thus, the techniques described herein employing nanochannels are also applicable to devices including microchannels. Some devices may include multiple nanochannels or microchannels, i.e., arrays. Some or all of the structures may also be sealed with a cap in order to provide closed channels.

Detector electrodes are fabricated, for example, according to any one of numerous metal deposition techniques suitable for fabrication of electrodes that exist in conventional microfabrication process flows. Each technique has positive and negative attributes and a list of the materials that may be deposited using that technique. The three primary techniques are: electron beam evaporation, thermal evaporation, and sputtering. The detector electrodes may have thicknesses ranging from 5 nanometer (nm) to 100 nm at the point where the electrodes intersect the fluidic channels. The electrodes may be wider and/or thicker in regions distal to the fluidic channels and approaching contact pads disposed at the perimeter of the device.

Fluidic channels may be formed in the substrate by, e.g., lithographic and etch steps. The substrate may be, e.g., a silicon-on-insulator wafer, with, for example, a (100) Si surface, a Si wafer, a fused silica, or a gallium arsenide substrate. Lithography in the sub-100 nm regime may be performed by various techniques, including the following: electron beam lithography (EBL), nanoimprint lithography (NIL) or deep ultraviolet optical lithography (DUV OL). See Liang, X.; Morton, K. J.; Austin, R. H.; Chou, S. Y., Single sub-20 nm wide, centimeter-long nanofluidic channel fabricated by novel nanoimprint mold fabrication and direct imprinting, Nano Lett. 2007, 7, 3774-3780; Austin, M. D.; Ge, H.; Wu, W.; Li, M.; Yu, Z.; Wasserman, D.; Lyon, S. A.; Chou, S. Y., Fabrication of 5 nm line width and 14 nm pitch features by nanoimprint lithography, App. Phys. Lett. 2004, 84, 5299-5301; and Guo, J., Recent progress in nanoimprint technology and its applications, J. Phys. D: Appl. Phys. 2004, 37, R123-R141, which are incorporated by reference herein in their entirety. The current industry standard in micro- and nanofabrication is optical lithography due to its low cost and high throughput. At present, optical lithography has been successfully used in the mass production of devices with critical dimensions as small as 32 nm. EBL and NIL are presently used extensively in academic research environments due to their versatility and capability of producing sub-10 nm features reproducibly. Any of these methods may be used to pattern the fluidic channels described herein.

The removal of material for the formation of the fluidic channels may be performed by, e.g., etching. Wet etching includes the immersion of the material in a solution capable of selective removal. Dry etching, i.e., reactive ion etching (RIE), involves the exposure of the sample to a charged plasma. For the resolution and control required of nanoscale fabrication, RIE is preferable due to its consistency, controllability, and efficiency. Microfluidic channels or reservoirs leading to the nanoscale channels may be etched using either wet or dry methods.

As stated previously, the fluidic channel may be a microchannel having a width selected from a range of about 1 µm to about 25 µm or a nanochannel having a width selected from a range of about 10 nm to about 1 µm. In the case of a microchannel, the depth may be selected from a range of about 200 nm to about 5 µm, whereas in the case of a nanochannel, the depth may be selected from a range of about 10 nm to about 1 µm. The fluidic channels may have a length selected from a range of, e.g., 1 micrometer (µm) to 10 centimeters (cm). It should be understood, however, that in each case presented herein, the dimensional ranges are intended to be exemplary only, and should not be considered as limitations.

To complete the device, a cap layer may be introduced to prevent evaporation of liquid from the fluidic channel. The cap may be formed over just the nanoscale fluidic paths or over all of the fluidic channels. In the latter case, the cap structure preferably has ports to allow for the introduction of fluid and samples into the fluidic paths, although such ports may also, or alternatively, be formed in the substrate as well. In another embodiment, the entire substrate, i.e., wafer, may be capped.

More particularly, an exemplary fabrication process for forming detector electrodes and defining the fluidic channel is as follows. A suitable substrate, such as a conventional (100) p-type silicon wafer, is thermally oxidized in a hydrated atmosphere to grow a thick (e.g., >1 µm) silicon-dioxide ($SiO_2$) or a silicon-nitride layer. This $SiO_2$/silicon nitride layer may serve as insulation between subsequently formed adjacent metal electrodes, and may also reduce overall device capacitance.

Embedded metal detector electrodes are fabricated, for example, using the conventional high resolution optical lithography that may be used to transfer the metal electrode pattern to a second photoresist masking layer. RIE with an anisotropic etch species, such as $CF_4$, may be used to transfer the pattern into the $SiO_2$/silicon nitride layer. The depth of these trenches may be less than, equal to, or greater than the depth of the fluidic channel. In one embodiment, the depth of these trenches exceeds or equals the depth of the fluidic channel. Upon completion of pattern transfer to the SiO$_2$/silicon nitride layer, a thin metal adhesion promotion layer may be deposited. A suitable layer is tantalum with a thickness of 30-50 Å, deposited via electron beam evaporation. Next, the electrode material is deposited without exposing the substrate to atmosphere. A preferred metal for the bulk of the electrodes is platinum, also deposited via electron beam evaporation. Other examples of suitable metals include gold, chrome, titanium, silver, and graphene. The thickness of the metal is dictated by the depth of the etched fluidic channels, such that the resultant metal trace is approximately planar with a top surface of the SiO$_2$/silicon nitride layer. Upon completion of the metal deposition, the substrate is immersed in a photoresist solvent that lifts-off excess metal from the surface and the substrate is vigorously cleaned. Chemical-mechanical polishing (CMP) may be performed to remove excess metal extending over the SiO$_2$/silicon nitride top surface, thereby planarizing a top surface of the metal to be level with the SiO$_2$/silicon nitride top surface.

Using conventional high resolution optical lithography, the pattern of the fluidic channel may be transferred to a first photoresist masking layer. RIE with an anisotropic etch species, such as CF$_4$, may be used to transfer the pattern into the SiO$_2$/silicon nitride layer to define a trench that functions as a fluidic channel in the completed device. The preferred width and depth of the fluidic channel may be determined by the requirements for the device sensitivity. The smaller the volume of the fluidic channel between two electrodes, the more sensitive the device is. Fluidic channel size, width, and depth, may also be determined by the size or behavior of the analyte. In one embodiment, the device described herein is used to detect strands of DNA. It may be desirable to fabricate the fluidic channel with dimensions that extend the DNA strand within the channel. For instance for double-stranded DNA, it has been found that the use of fluidic channels with dimensions of 100 nm or less are able to extend the biomolecule. See Tegenfeldt, J. O et al. *The dynamics of genomic-length DNA molecules in 100-nm channels*. Proc. Nat. Acad. Sci. USA, 2004, 101, 10979-10983, which is incorporated by reference herein in its entirety. Upon completion of the dry etch procedure, residual resist is removed and the substrate vigorously cleaned.

To complete the fabrication of the device, a cap layer is preferably adhered to the device surface to provide a leak-free seal, enabling fluidic conduction. Preferred cap materials include borosilicate glass, fused silica, fused quartz, quartz, phosphosilicate glass, or other suitable materials. Various techniques are suitable for affixing the cap, including anodic bonding. In anodic bonding, an underlying silicon wafer and a glass substrate are pressed together and heated while a large electric field is applied across the joint. Anodic bonding has been demonstrated to form a strong bond between a silicon wafer and the capping substrate. Direct silicon bonding has been used to join two silicon wafers. The latter method involves pressing the two wafers together under water. Other methods use an adhesive layer, such as a photoresist, to bond the cap to the substrate.

Ports may be created in the cap layer or the underlying substrate to provide access to fluidic inlets, fluidic outlets, and electrodes. A typical method for forming ports in glass wafers is ultrasonic etching, which allows for highly controllable pattern transfer to glass substrates.

It is intended that the above description of device fabrication is intended only to be illustrative, and numerous other techniques for forming micro/nano fluidic devices having embedded micro/nano electronic circuitry will be apparent to those having ordinary skill in the art.

An exemplary device with a pair of such nanoscale detector electrodes, i.e., electrodes 115A, 115B, is illustrated in FIG. 2. Electric current is transferred in the form of ionic flow in an electrolyte solution confined in the fluidic channel (e.g., a nanochannel). The electrolyte serves to maintain a uniformly distributed electric field in the fluidic channel and acts as a medium in which the target analytes are carried. Typical electrolyte solutions have been described in applications of electrophoresis to separations of DNA molecules. Electrolytes suitable for electrophoretic separation of DNA are Tris boric acid EDTA (TBE) and tris acetate EDTA (TAE). See, e.g., Sambrook, J.; Russell, D. W. *Molecular Cloning: A Laboratory Manual* 3$^{rd}$ ed. Cold Spring Harbor Press, 2001, which is incorporated by reference herein in its entirety. Other conductive media may be used.

Figure 3:
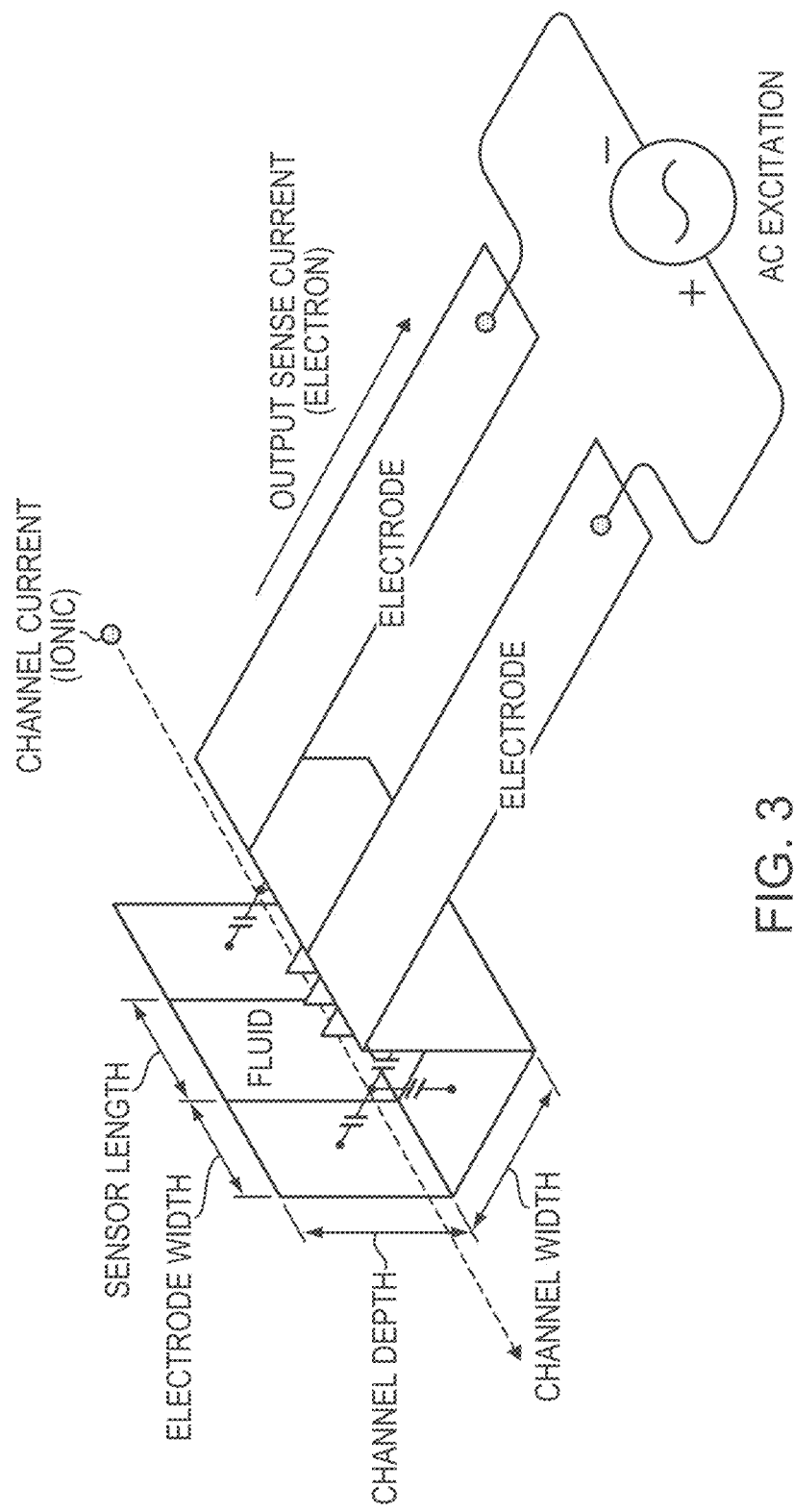
FIG. 3 is a schematic drawing of one embodiment of the invention featuring an alternating current (AC) excitation-induced potential applied across a detection volume.

FIG. 3 provides another view of the simplified hybridization assisted nanochannel sequencing apparatus shown in FIG. 2, including a signal source 120 that provides an AC voltage across the detection volume. Current is driven through double layer capacitances (depicted figuratively in FIG. 3 as capacitors) into the fluid in the channel between the detector electrodes. The net potential "seen" by the fluid within the volume defined by the sensing electrode pair is the superposition of the AC voltage and the DC potential gradient applied via electromotive electrodes at either end of the channel (not shown in FIG. 3). The electric field that is applied to the channel via the electromotive electrodes is substantially isolated from, and independent of, the excitation signal applied to the detection volume. Furthermore, the resistance of the detection volume (depicted figuratively in FIG. 3 as a resistor) varies depending on whether the analyte is present within the detection volume, and whether that portion of the analyte within the detection volume includes a hybridized probe. Thus, by measuring voltage or current using the detector electrodes, it is possible to distinguish between three possible states of a given detection volume, as a function of time: (i) where there is no analyte in the detection volume; (ii) where there is a portion of the analyte in the detection volume without a hybridized probe; and (iii) where there is a portion of the analyte in the detection volume having a hybridized probe.

Figure 4A:
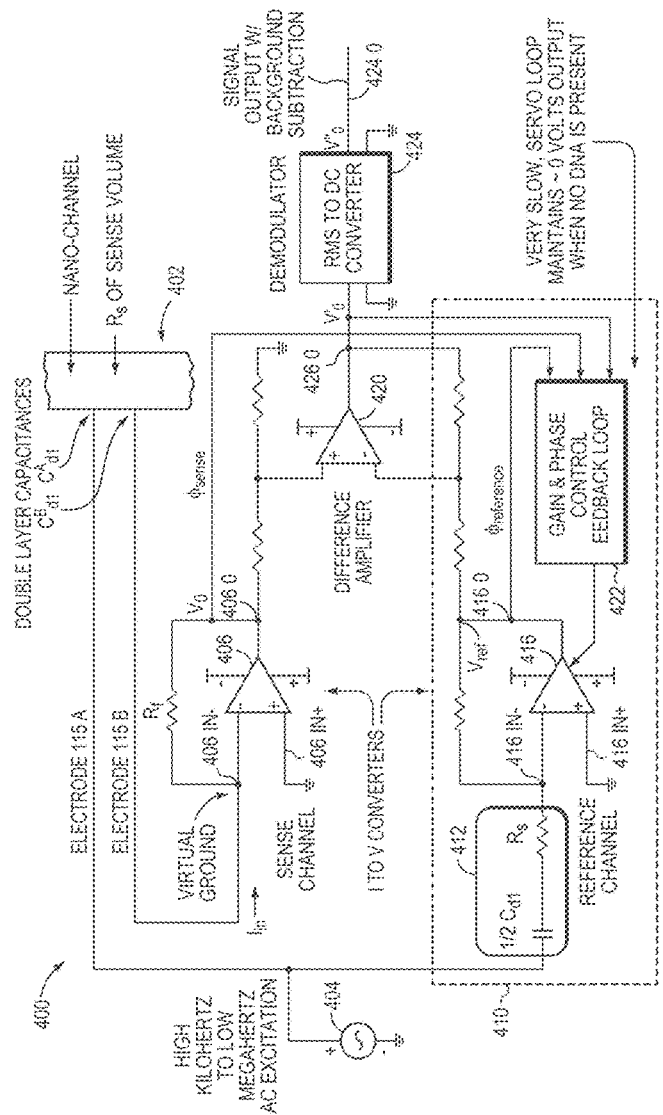
FIG. 4A is a schematic drawing of circuitry for the apparatus of an embodiment of the invention shown in FIG. 3.

FIG. 4A depicts one embodiment of a system 400 for applying an AC voltage excitation signal from signal source 404 across a detection volume 402, and measuring and processing the corresponding output signals. The detection volume 402 is the volume of the fluid in the fluidic channel or pore 105 located between the electrodes 115A, 115B. The detection volume 402 may be characterized by double-layer capacitances $C^A_{dl}$, $C^B_{dl}$, and a resistance $R_s$. The signal source 404 supplies an AC voltage signal having fixed or adjustable frequency, preferably in the range of about 10 kHz to about 50 MHz. In certain embodiments, the frequency is in the range of about 10 kHz to about 5.5 MHz, and in other embodiments, the frequency is in the range of about 5 MHz to about 50 MHz. The peak-to-peak amplitude of the signal may be fixed or adjustable and may range, for example, from 0.5 to 5 Vpp (volts peak-to-peak). One terminal of the signal source 404 is in electrical communication with the electrode 115A, and the other terminal of the signal source 404 is connected to ground.

The electrode 115B is in electrical communication with the inverting-input 406IN− of an operational amplifier ("op-amp") 406. The non-inverting input 406IN+ of the op-amp 406 is connected to ground, and the output terminal 406O of the op-amp 406 is connected to the inverting input 406IN− via a resistor $R_f$. Accordingly, the op-amp 406 is configured as a current-to-voltage ("I-to-V") converter, i.e., the voltage $V_o$ produced at the output node 406O is substantially determined by $R_f$ times the current $I_{in}$ flowing into the inverting input 406IN−. In other embodiments, devices such as field-effect transistors (FETs), bipolar junction transistors (BJTs), and/or heterojunction bipolar transistors (HBTs) may be configured as I-to-V converters.

The resistance $R_s$ of the detection volume 402 varies depending on whether an analyte is present within the detection volume 402. When an analyte is not present within the detection volume 402, the value of $R_s$, denoted as $R^c_s$, is relatively low compared to the value of $R_s$ when an analyte is present within the detection volume. $R^c_s$ is typically in the range of approximately 0.5 MΩ up to approximately 5 MΩ, and may be called the nominal channel resistance, i.e., the resistance of the detection volume without an analyte present therein. The capacitance of the double-layer capacitors $C^A_{dl}$, $C^B_{dl}$ generally depends on the geometry of the detector electrodes 115A, 115B, and is on the order of 200 to 1000 femto Farads. Due to the relatively low $R^c_s$, the current $I_{in}$ produced by the excitation signal supplied by the signal source 404 has a relatively high RMS amplitude, denoted as $I_{high}$ (e.g., approximately in the range 0.5 to 4.5 µA). Correspondingly, the voltage $V_o$ at the output node 406O of the op-amp 406 is produced at a level denoted as $V_1$. It must be noted that all voltages and currents discussed in the text are of the form $V_N \sin(2\pi f_c t + \theta)$, where $V_N$ is the amplitude of the voltage signal (resulting in a DC/non-alternating signal $V_0$, $V_1$, etc., after manipulation in which the carrier wave has been eliminated), $f_c$ is the carrier frequency of the excitation, and $\theta$ is a phase. The range of values of the level $V_1$ is determined by the parameters of various circuit components such as the value of the resistor $R_f$, the gain of the op-amp 406, etc. As explained below, not the actual values of the level $V_1$, but a change in $V_o$ from the level $V_1$ to another level (described below) may be used to detect the presence of a portion of the analyte in the detection volume 402.

When an analyte enters the detection volume 402, the resistance $R_s$ typically increases, but by a very small amount $\Delta R_s$, for example, by about 0.1% or 0.2% of $R^c_s$, i.e., the nominal channel resistance. The increased $R_s$ is denoted as $R^a_s$. Because the AC excitation signal supplied by the signal source 404 remains substantially unchanged in terms of frequency and the RMS voltage, the increase in the value of $R_s$ causes the RMS amplitude of the current to decrease to a value denoted as $I_{mid}$. As a result, the voltage $V_o$ at the output terminal 406O changes to a level denoted as $V_2$. If a probe is hybridized to the portion of the analyte within the detection volume, the value of $R_s$ increases even further. As before, however, this increase is also very small, for example, about an additional 0.025% or 0.2% of $R^c_s$. This can cause the current $I_{in}$ to decrease further, and the voltage $V_o$ to change to another level denoted as $V_3$. By observing and comparing the values of $V_o$ (or corresponding current) over time, the absence or presence of an analyte in the detection volume 402, and the presence of a probe hybridized to a portion of the analyte can be detected. As described elsewhere herein, coatings and or tags may be attached or otherwise applied to the analyte (and/or probe) in order to enhance the detectable signal.

As described above, typically the difference in the values of $R_s$ when an analyte is not present in the detection volume 402, (i.e., $R^c_s$) and when a portion of the analyte without a hybridized probe is present in the detection volume 402, (i.e., $R^a_s$) is very small compared to the value of $R^c_s$, i.e., in the range of about 0.1% to 0.2% of $R^c_s$, or from about 500Ω up to about 10 kΩ. Correspondingly, the difference between $V_1$, i.e., $V_o$ when the analyte is not present in the detection volume 402, and $V_2$, i.e., $V_o$ when a portion of the analyte without a probe hybridized thereto is present in the detection volume 402, is also very small relative to $V_1$. Similarly, the difference in the values of $R_s$ due to the presence within the detection volume 402 of a portion of the analyte with a hybridized probe, denoted as $R^p_s$, and due to the presence within the detection volume of a portion of the analyte without a probe, i.e., $R^a_s$ is also very small, e.g., about 0.125 to 0.4% of $R^c_s$. Therefore, the difference between $V_3$, i.e., $V_o$ when a portion of the analyte with a probe hybridized thereto is present in the detection volume 402, and $V_2$, is also very small. Put simply, $V_3 > V_2 >> V_1 \geq V_0$.

Because of the small variation in each of the two difference values described above, i.e., $(V_2 - V_1)$ relative to $V_1$, and $(V_3 - V_2)$ relative to $V_2$, it is desirable that circuitry designed for distinguishing between the absence and presence of an analyte in the detection volume 402, and for distinguishing between an analyte without a hybridized probe present within the detection volume 402 and an analyte with a hybridized probe within the detection volume 402, be highly sensitive to small fractional changes in the voltage $V_o$ at the terminal 406O of the op-amp 406.

Such high sensitivity can be provided by effectively storing the background signal, $V_1$, by way of long (i.e. the entire time that the analyte is in the sense volume) time constant control loops or low pass filters, and subsequently subtracting it from $V_o$ (which is comprised of signal and background) which allows significant gain to be inserted in the signal path which would not be possible if the large background signal were present. As described above, when an analyte is not present in the detection volume 402, the voltage $V_o$ at the terminal 406O of the op-amp 406 is substantially at the level $V_1$. Therefore, by subtracting $V_1$ from $V_o$, a subtractor (described below in detail) can produce a signal at approximately 0 V when an analyte is not present in the detection volume 402. When a portion of the analyte without a hybridized probe is present in the detection volume 402, $V_o$ may change to $V_2$, and correspondingly, the output of the subtractor would change to approximately $V_2 - V_1$. This difference, though small, can be distinguished from the previous approximately 0 V output of the subtractor, and thus, the presence of a portion of an analyte without a hybridized probe in the detection volume 402 can be detected.

If a portion of the analyte having a hybridized probe enters the detection volume 402, the difference $V_3 - V_2$, though small, can be distinguished. Thus, the presence of a portion of an analyte with a hybridized probe in the detection volume 402 can be detected. The presence of another analyte, without or with a probe attached thereto, can then be detected as described above. In order to provide the voltage level $V_1$ for subtraction from $V_o$ (i.e., the output voltage of the op-amp 406) as described above, the system 400 includes a reference generator 410 that produces a signal $V_{ref}$ that estimates $V_1$, as further explained herein below.

The AC voltage excitation signal produced by the signal generator 404 is supplied to a resistance-capacitance (RC) circuit 412 included in the reference generator 410. The value of the capacitance in the RC circuit 412 is approximately equal to $\frac{1}{2} C_{dl}$ where the value of $C^A_{dl}$ and $C^B_{dl}$, each is about $C_{dl}$. The value of the resistance in the RC circuit 412 is approximately equal to $R^c_s$. Therefore, the RC circuit 412 substantially mimics the resistance-capacitance characteristic of the detection volume 402 when an analyte is not present therein. It is noted that the RC circuit may be an integrated structure on the same silicon chip that contains the detector, or alternatively, it could be external to the chip. This latter instance allows for a more practical value of C to be selected along with a suitable R that would, at the operating carrier frequency, produce a reference channel phase shift that nominally matches the phase shift of the actual sensor.

Because the same excitation signal that is supplied to the detection volume 402 is also supplied to the RC circuit 412, a current of about the same value as $I_{high}$ flows into an inverting input 416IN− of an op-amp 416 configured as an I-to-V converter. Accordingly, the output voltage at the node 416O, denoted as $V_{ref}$, can be about the same as $V_1$ if the gain of the op-amp 416 is about the same the gain of the op-amp 406. If, as described in one embodiment above, the RC circuit is external to the chip including the detector, the I-to-V converter of op-amp 416 is scaled such that $V_{ref}$ nominally matches $V_o$ with no analyte present.

The output node 406O is in electrical communication with one input of a difference amplifier 420, and the output node 416O is in electrical communication with another input of the difference amplifier 420. The difference amplifier 420 produces a signal, denoted as $V'_o$, at an output node 420O, representing a difference between the voltages received at the two inputs. In one embodiment, the difference amplifier is an op-amp, and the output nodes 406O, 416O are connected to the non-inverting and inverting terminals of the op-amp 420, respectively. As a result, a voltage ($V_o-V_{ref}$) is produced at the output node 420O.

It should be understood that it is relatively easy to ensure that the respective gains of 406O and 416O are virtually identical. Thus, the reference channel is intended to address the issue that $R_s$ and $C_{dl}$ in the main channel are strong functions of channel geometry, electrolyte chemistry, temperature and time. Thus, one cannot simply rely upon a structure such as RC circuit 412 and expect of to achieve adequate baseline subtraction performance. Ideally, the reference channel is an essentially identical fluidic channel to the sensing channel or a structure having the same properties, including temperature dependence. While the embodiment described assumes that an on-chip RS structure could be synthesized to provide a nominal match to a specific channel, it is intended that the gain and phase feedback loop 422 described below would be responsible for compensating for initial inaccuracies and for tracking and compensating for subsequent changes in variables such as time, temperature and electrolyte chemistry and the like.

Another embodiment that would enable the reference channel to achieve ~0 volts output when no analyte is present would be to input the excitation signal itself into a phase locked loop, controlled via slow gain & phase feedback loops derived from the output of difference amplifier 420. These would be too slow to respond to the relatively fast transient DNA events yet fast enough to track and cancel time, temperature & chemistry effects.

To facilitate an accurate differencing (i.e., subtraction) of the AC signals $V_o$, $V_{ref}$, their phases must be aligned and the outputs of the op-amps 406, 416 must be approximately the same. Such gain and phase adjustment is provided by the gain and phase control module 422, which receives the signals $V_{ref}$, $V_o$, and $V'_o$. Using the information about the phases and amplitudes of the received signals, the gain and phase control module 422 can adjust the gain of the op-amp 416 such that $V'_o$ is approximately 0 V when no analyte is present in the sense volume 402, as depicted at 451 in FIG. 4B.

Figure 4B:
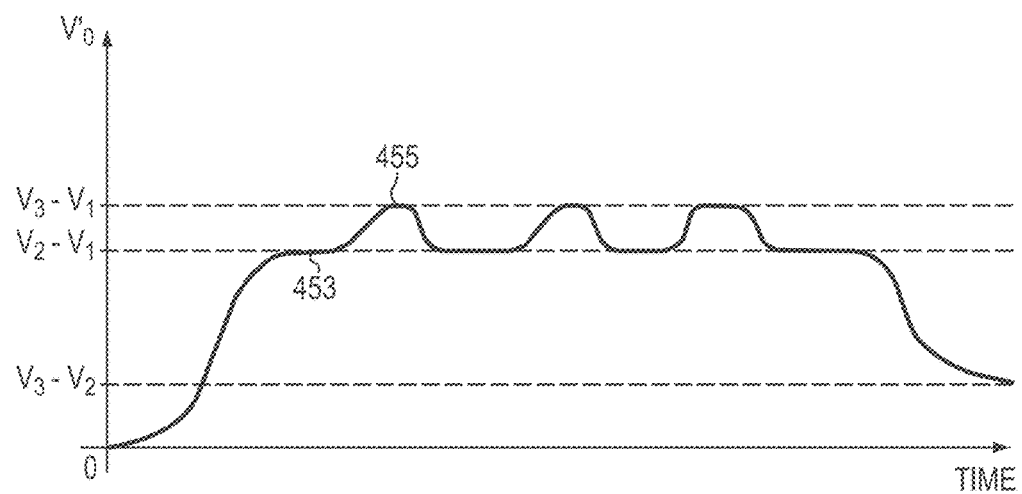
FIG. 4B depicts an exemplary signal produced during the operation of the circuitry illustrated with reference to FIG. 4A.

With reference to FIG. 4B, when a portion of an analyte without a hybridized probe enters the detection volume 402, $V_o$ changes to $V_2$ and, accordingly, $V'_o$ changes to $V_2-V_1$, as described above and as shown at 453. This value of $V'_0$ can be distinguished from approximately 0 V, and thus, the presence in the detection volume 402 of an analyte without a hybridized probe can be detected. When a portion of the analyte with a hybridized probe enters the detection volume 402, $V'_0$ changes further to $V_3-V_1$, as described above and shown at 455.

In practice, for most of the time, no analyte, whether with a hybridized portion or not, is present in the detection volume of the detector, (i.e., the time between detection events is long and the duration of detection events is short). Thus, the steady state output at $V_{ref}$ represents the baseline or zero reference of the detector for the temperature & chemistry conditions that exist at the time immediately prior to, and essentially remain constant throughout the time that, the analyte enters and leaves the detection volume. Temperature and chemistry induced shifts in the baseline are gradual, slow and thus continuously tracked and cancelled by the slow feedback loops. Thus, the output at $V'_0$ only responds to signals resulting from the presence of an analyte, either with or without a hybridized probe in the detection volume. If the bandwidth required to track temperature and time variations is slow relative to the time that the analyte is in the channel, i.e., minutes for slow effects and milliseconds for analyte events, time constants for the servo-loops may be set such that sag is reduced to effectively zero.

In other words, as an analyte enters the detection volume 402, voltage $V'_0$ starts at zero (as a result of the baseline subtraction described above) and rises by an amount (ΔV) that is proportional to the fluid that is displaced from the sense volume due to the presence of the analyte. If a portion of the analyte includes a hybridized probe, when that hybridized portion enters the detection volume, voltage $V'_0$, already at a level determined by the sensed unhybridized portion of the analyte, rises incrementally above the analyte signal by a further ΔV proportional to the additional fluid that is displaced from the sense volume by the hybridized probe. Once the portion of the analyte having the hybridized probe leaves the sense volume, $V'_0$ returns to the value corresponding to the presence of analyte only. Finally, once the analyte exits the detection volume entirely, voltage $V'_0$ returns to the original baseline (which should be essentially still at zero) minus any small sag in $V_{ref}$ which may have occurred.

It should be understood that the configuration and operation of the phase and gain control module 422 described herein is illustrative only, and that in some embodiments, the module 422 may adjust $V_{ref}$ (i.e., the output of the op-amp 416) to $V_1$ only, and not to $V_2$. In other embodiments, the phase and gain control module 422 may not even be used. For example, an alternate way to achieve a $V'_0$ approximating zero when no analyte is present would be to input excitation signal 404 into a phase locked loop functional block whose output would be controlled via slow gain & phase feedback signals derived from the output of difference amplifier 420. One would select the difference amplifier to be too slow to respond to the relatively fast transient detection events yet fast enough to track and cancel time, temperature & chemistry effects.

In general, using the reference generator 410, the difference amplifier 420, and the phase and gain control module 422, a large offset voltage of about $V_1$ volts caused by the fluid being tested is substantially eliminated from $V'_o$ (i.e., the signal at the output node 420O). Therefore, $V'_0$ only varies in a range of about 0 volts up to about $V_3$ volts. Since the difference amplifier 420 only responds to the difference signal applied to its inputs, and the reference channel essentially removes the very large steady state component of the signal, difference amplifier 420 can have significantly higher gain, thus making detection of the absence or presence of an electrolyte, with or without a probe, robust.

The value of $V_1$ (i.e., the voltage at the output node 406O when analyte is not present in the detection volume 402), however, may change over time due to changes in properties of the fluid in the channel 105 such as its temperature, chemical properties, and the like. Unless $V_{ref}$(i.e., the output at the node 416O) is adjusted according to the changes in $V_1$, the output $V'_o$ would not remain substantially at 0 V when an analyte is not present in the detection volume 402. This may cause an erroneous false detection of the presence of an analyte or cause saturation of difference amplifier 420.

This error is also mitigated or eliminated by the phase and gain control module 422. As described above, the module 422 receives the signals $V_o$, $V_{ref}$, and $V'_o$, i.e., the outputs at the nodes 406O, 416O, and 420O, respectively. By comparing these values, the phase and gain control module 422 determines if $V_1$, as represented by $V_o$, has drifted and accordingly adjusts a gain of the op-amp 416. This causes $V_{ref}$ to be adjusted such that the modified $V_{ref}$ is substantially the same as the new value of $V_1$. In turn, the output $V'_o$ at the node 420O remains substantially at 0 V when an analyte is not present in the detection volume 402. It should be understood that the symbol represented by op-amp 416 need not be a simple op-amp but rather, may be a function block realized by one or more op-amps or other circuitry. It is intended that the function performed by blocks 422 and 416 is to produce an output at $V_{ref}$ that is substantially identical to $V_o$ by continuously tracking $V'_o$ and driving it to zero.

The signal generator 404 applies an AC excitation signal to both the detection volume 402 (via detector electrode 115A) and the reference generator 410. Therefore, the signals $V_o$, $V_{ref}$, and $V'_o$ are also AC signals. Because the double layer capacitance at the electrode/fluid boundary may prevent DC current from flowing, and, therefore, may prevent detection of analyte, with or without a hybridized probe, an AC excitation signal is used in order to cause current to flow in the sense volume and allow detection to occur. The AC component of the signal, commonly referred to as the carrier, only provides the means for current to flow through the sense volume, so its frequency and or phase actually contains no useful information as to the presence or absence of analyte whether or not the analyte includes a hybridized probe. The carrier frequency is typically selected to be much higher than the highest frequencies contained in the signal of interest, therefore, sense volume detection information is contained only in the amplitude of the carrier signal. While the AC signals $V_o$ and $V'_o$ can be directly measured to detect the absence or presence of an analyte in the detection volume, whether or not it includes a hybridized probe, AC measurements of very small changes of amplitude are difficult. Since the carrier frequency is quite high relative to the detection signal, it is possible to remove the carrier signal leaving only the desired detection information.

Figure 4C:
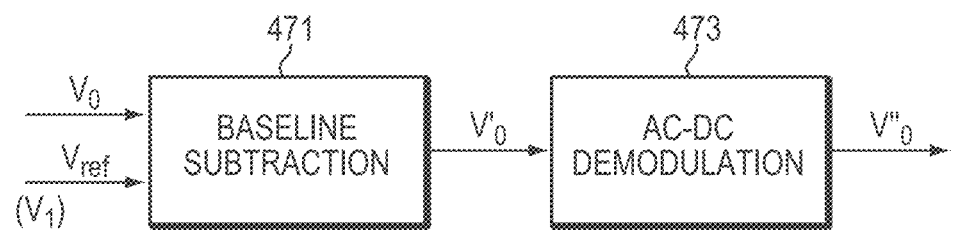
FIG. 4C schematically shows one order of certain operations performed by circuitry of the apparatus shown in FIG. 3, according to one illustrative embodiment of the invention.

Therefore, in the system 400, the output 420O is in electrical communication with a demodulator 424 that strips off the high frequency carrier and extracts the desired detection signal values represented by $V'_o$. Specifically, the demodulator 424 is an AC to RMS converter that extracts the root-mean-squared (RMS) value of the AC signal $V'_o$, and produces an output voltage $V''_o$ that represents the extracted RMS value, at a node 4240. Alternatively, envelope detection methods may be employed to achieve AC demodulation. By selecting appropriately the bandwidth of the AC to RMS function in demodulator block 424, the RMS output $V''_o$ will respond to the detection information contained in signal $V'_o$ while rejecting the high frequency carrier signal. In this configuration, shown schematically in FIG. 4C, a "baseline voltage," i.e., the voltage $V_1$ is first subtracted at 471 from the output of the I-to-V converter 406. Then, demodulation of the signal V'o is performed at 473 to produce V''o. When V''o is greater than 0 V, since the phase and gain control module 422 has maintained $V_{ref}$ substantially to $V_1$, the presence of an analyte or analyte having hybridized probe is detected in the sense volume 402, the magnitude change in $V''_o$ above zero will determine if the analyte alone or analyte with hybridized probe is present in the sense volume. As noted previously, $V''_o$ will exhibit an increase in response to the presence of an analyte in the sense volume and will exhibit a further increase when a portion of the analyte having hybridized probe is present in the detection volume. Once the portion of the analyte having the hybridized probe exits the detection volume, $V''_o$ will recede to a level corresponding to the presence of analyte without a hybridized probe. This action will continue as additional probes pass through the sense volume. When the analyte completely exits the sense volume, $V''_o$ will decrease back to approximately zero minus any sag in the background subtraction circuit.

Figure 4D:
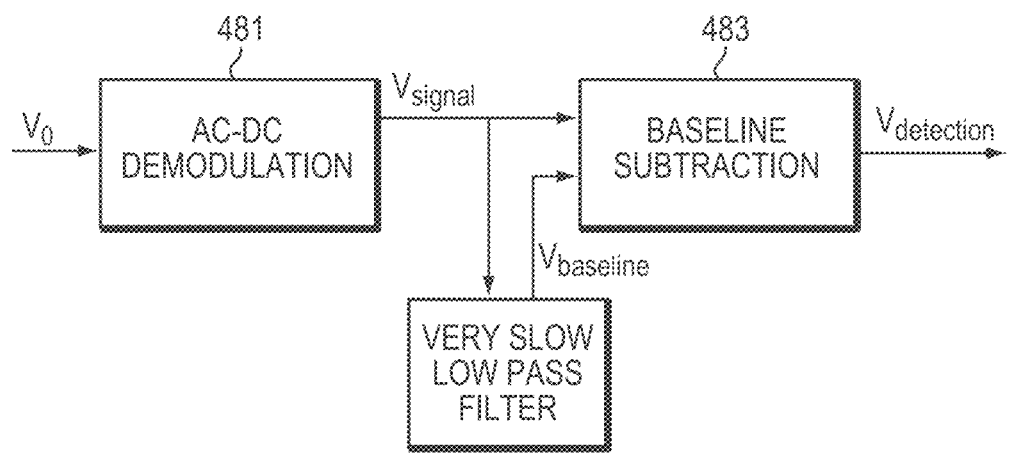
FIG. 4D schematically shows one order of certain operations performed by circuitry of the apparatus shown in FIG. 3, according to another illustrative embodiment of the invention.

With reference to FIG. 4D, $V_o$, i.e., the signal at the output of the op-amp 406 which comprises a detection signal, a carrier signal and a baseline signal, is first converted at AC demodulator 481 to produce $V_{signal}$ comprising the detection and baseline signals. $V_{signal}$ is split to run through a low pass filter to determine $V_{baseline}$, i.e., the baseline signal, and to run through a baseline subtractor 483. The resulting signal $V_{detection}$ comprises the desired, information-carrying signal indicative of whether (i) no analyte is present in the detection volume; (ii) a portion of the analyte lacking a hybridized probe is present in the detection volume; and (iii) a portion of the analyte having a hybridized probe is present in the detection volume.

In alternative embodiments, instead of using a current-to-voltage converter such as the converter 406 of FIG. 4A, the current $I_{in}$ may measured and analyzed directly, to determine the absence or presence of an analyte in the detection volumes. In other embodiments, a voltage across the electrodes 115A, 115B, FIG. 2, may also be measured and analyzed directly.

Figure 5A:
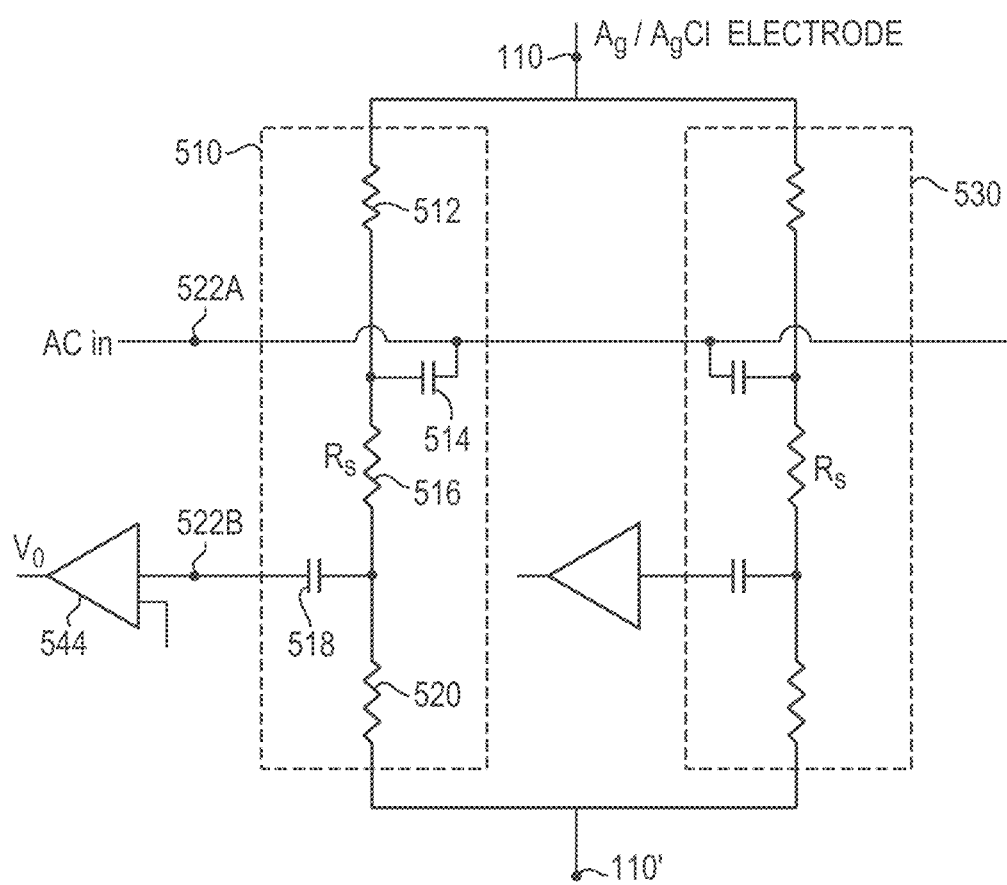
FIG. 5A is a schematic drawing of circuitry for the apparatus shown in FIG. 3, including resistance and capacitance presented by the liquid in the channel and accounted for in the interpretation of detected signals, according to one illustrative embodiment of the invention.

A detection volume defined by the detector electrodes can be characterized as an RC circuit. With reference to FIG. 5A, the RC circuit 510 characterizing a first detection volume includes a resistor 512, representing the resistance of the fluidic channel from the first translocation electrode 110 to the first sensing electrode 115A (see FIG. 2). The capacitors 514 and 518 represent double-layer capacitance between, respectively, electrode 115A and fluidic channel 105, and electrode 115B and fluidic channel 105 (see FIG. 2). The resistor 516 represents the resistance of the fluidic channel within the detection volume defined by the sensing electrode pair 115A, 115B (see FIG. 2). Finally, a resistor 520, represents the resistance of the fluidic channel from the second sensing electrode 115B to the second translocation electrode 110' (see FIG. 2).

As described above, the AC voltage excitation signal is supplied to the detection volume via the first detection electrode 115A at node 522A, and sensed using an I-to-V converter 524 in electrical communication with the detection volume at node 522B, via detection electrode 115B. Thus, the excitation signal is substantially affected by the capacitors 514, 518, and the resistor 516, but not by the resistors 512, 520. Because the excitation source provided at node 522A is high frequency AC, sufficient current flows through the capacitors 514, 518 and the sense volume represented by resistor 516, that signal can be sensed at node 522B which would not be the case if DC, or low frequency AC, were used as an excitation source. The AC signal also does not noticeably affect the drive bias supplied by the translocation electrodes 110, 110'.

In general, the values of the capacitors 514, 518 vary according to the properties of the fluid in the fluidic channel 105 and the size and/or shape of the detector electrodes 115A, 115B, and do not change in response to the absence or presence of an analyte in the detection volume. As described above, the presence of a portion of an analyte (with or without a hybridized probe) displaces fluid from any given volume and thus causes the resistance of that volume to change. Accordingly, if an analyte is present in the channel outside the detection volume, the values of the resistors 512 or 520 may change, but these resistors do not substantially affect the excitation signal.

On the other hand, if the analyte is present within the detection volume, the value of the resistor 516 (i.e., $R_s$) may change, affecting the detected signal, e.g., the current passing through the node 522B may decrease. Thus, it is possible to determine whether a portion of the analyte is present in the detection volume and, if so, whether or not a probe is hybridized to the analyte portion using an AC excitation signal supplied at the node 522A and sensed at the node 522B. The RC circuit 530 (as shown in FIG. 5A) shows various resistors and capacitors associated with a second detection volume, which may correspond to the same pore/nano-channel or a different one, as explained below with reference to FIGS. 7-9.

Figure 5B:
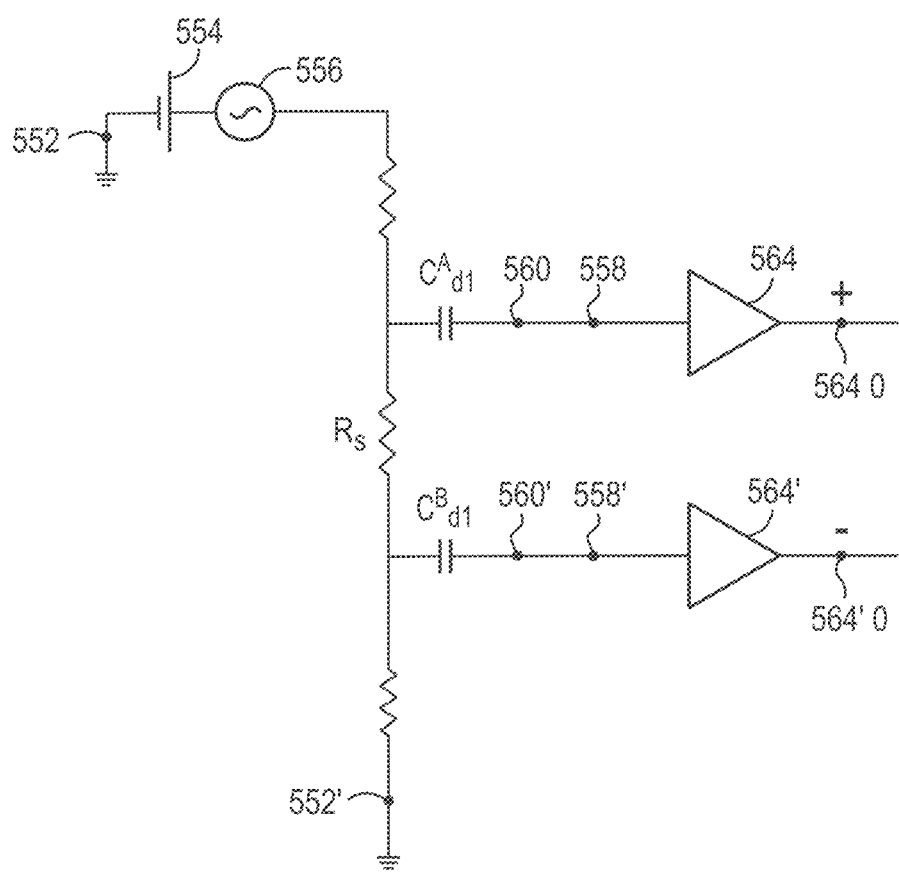
FIG. 5B is a schematic drawing of circuitry for the apparatus shown in FIG. 3, including resistance and capacitance presented by the liquid in the channel and accounted for in the interpretation of detected signals, according to another illustrative embodiment of the invention.

With reference to FIG. 5B, the translocation electrodes 552, 552' provide both a DC signal 554 for translocation of the analyte, and an AC voltage excitation signal 556. In this embodiment, the detector electrodes 558, 558' are only used for sensing and are not used to provide the AC excitation signal. One terminal of the sense electrode 558 is in electrical communication with one end 560 of the sense volume (characterized by the double layer capacitors $C^A_{dl}$, $C^B_{dl}$, and a resistance $R_s$). The other terminal of the sense electrode 558 is in electrical communication with an amplifier 564. In this case, the voltage in the detection volume where the electrode is in contact with the fluid in the detection volume would be sensed, as opposed to sensing the current. Similarly, one terminal of the detector electrode 558' is in electrical communication with the other end 560' of the fluid in the detection volume. The other terminal of the detector electrode 558' is in electrical communication with another amplifier 564'.

The voltage difference between the output terminals 564O, 564'O of the amplifiers 564, 564', respectively, represents a voltage difference across the detection volume. This voltage difference depends on the value of $R_s$, which changes depending on whether an analyte is present in the detection volume, and if the analyte is present, whether a probe is hybridized to that portion of the analyte in the detection volume, as described above. Therefore, a change in the voltage difference between the output terminals 564O, 564'O can be used to detect the presence of an analyte in the detection volume, and to detect whether a probe is hybridized to the analyte present in that portion of the analyte in the detection volume, as described with reference to FIG. 4A.

Figure 6:
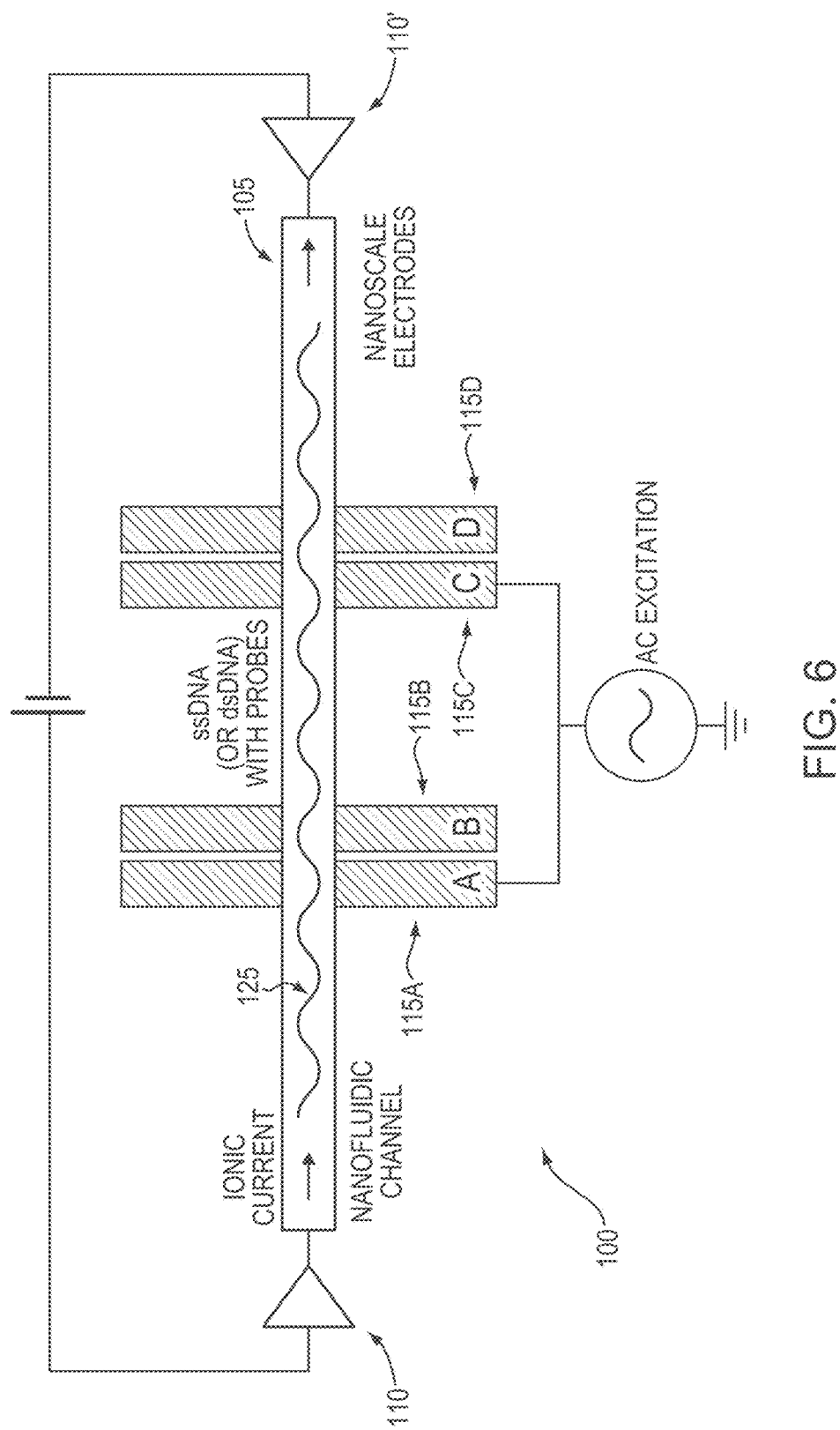
FIG. 6 is a schematic drawing of the inventive apparatus featuring two pairs of electrodes defining two detection volumes, according to another illustrative embodiment of the invention.
Figure 7:
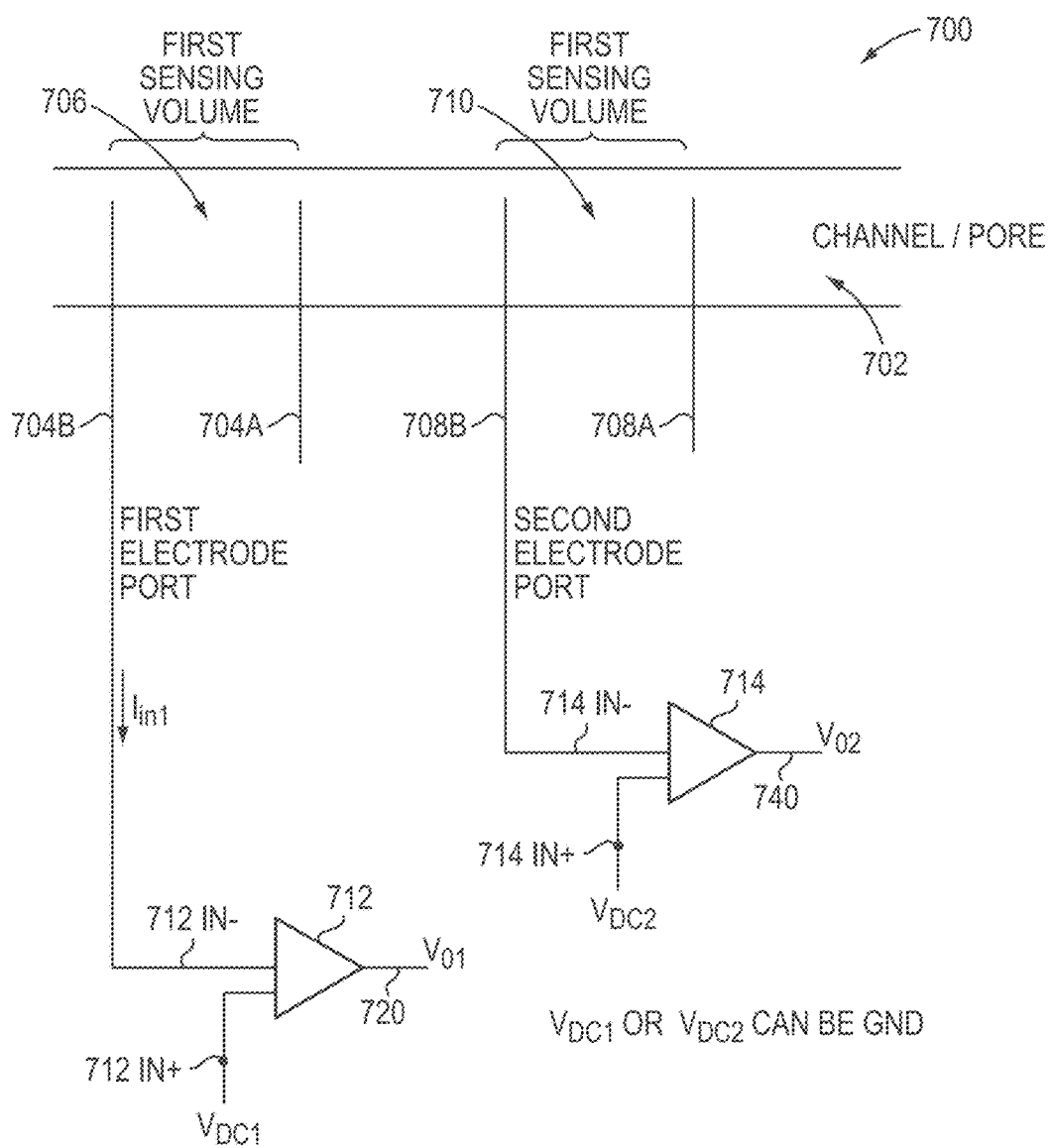
FIG. 7 is a schematic drawing of circuitry for the apparatus shown in FIG. 6, according to one illustrative embodiment of the invention.

The accuracy of detecting an analyte, either with or without hybridized probes, in embodiments of the present invention as described above with reference to FIG. 4A can be improved by any one or more of the following: (a) defining more than one detection volume in the pore or channel; (b) detecting an analyte as it translocates sequentially through each detection volume; and (c) statistically analyzing (e.g., averaging) the detection results. For example, FIG. 6 is a schematic drawing of an embodiment of a biomolecule analysis apparatus featuring two pairs of electrodes defining two detection volumes within a nanochannel. Two pairs of detector electrodes, 115A/B and 115C/D, are disposed along the fluidic channel 105, with a pair of electromotive electrodes 110, 110' at the ends of the channel. Additional detail regarding the detector electrodes and associated circuitry is shown in FIG. 7.

In the system 700 illustrated with reference to FIG. 7, in the fluidic channel 702, an electrode pair 704A, 704B defines a first detection volume 706. Another electrode pair 708A, 708B defines a second detection volume 710. An AC excitation signal source (not shown) supplies an excitation signal to the first detection volume 706 via the electrode 704A. The electrode 704B is in electrical communication with an inverting input node 712IN− of a current-to-voltage (I-to-V) converter 712. A bias DC voltage $V_{DC1}$ is supplied to the non-inverting input node 712IN+ of the I-to-V converter 712. The current at the input node 712IN− changes according to the absence or presence of a portion of an analyte in the detection volume 706, and whether a probe is hybridized to that portion, as described with reference to FIG. 4A. The voltage $V_{o1}$ at the output node 712O of the I-to-V converter 712 is substantially inversely proportional to $L_{in1}$.

Applying $V_{DC1}$, which may be different than the ground potential, to one input of the I-to-V converters has many benefits. For example, choosing $V_{DC1}$ to be substantially similar to the potential of the electrolyte inside the nanochannel at the position of the electrode can effectively force the DC voltage across the double layer capacitor at the electrode-electrolyte interface to be 0 V, which generally reduces potential negative effects such as leakage currents and noise generation. In addition, by suitably choosing a $V_{DC1}$, a target voltage drop across the double layer capacitor can be created and, depending on the polarity, this may result in the accumulation of positive or negative ions/charges inside the channel at the electrode position, altering the electric field distribution. This in turn, has potentially desirable effects such as affecting the motion of the target analyte molecules.

The same or a different AC excitation signal source may supply an excitation signal to the second detection volume 710 via the electrode 708A. Similar to the I-to-V converter 712, an I-to-V converter 714 in electrical communication with the second detection volume 710 generates a voltage signal $V_{o2}$ at the output node 714O that is substantially inversely proportional to the current at the inverting input node 714IN−. The non-inverting input 714IN+ of the I-to-V converter 714 is provided with a bias DC voltage $V_{DC2}$, and hence, $V_{o2}$ includes an offset of about $V_{DC2}$. $V_{DC2}$ may be different than $V_{DC1}$ because it is relative to a potential with a different magnitude occurring inside the nanochannel at a different electrode location.

In general, if an analyte passes through the first detection volume 706, it will also pass through the second detection volume 710. Therefore, both $V_{o1}$ and $V_{o2}$ should reflect the presence of the analyte as well as any hybridized probes. By comparing the detection results, for the same analyte, traveling sequentially through more than one detection volume within the same channel, detection errors can be reduced. Thus, by using more than one detection volume (e.g., the volumes 706, 710), redundant measurements are obtained and it is possible to determine with higher accuracy, at any given time during translocation, whether a portion of the analyte is present in the detection volume and, if so, whether or not a probe is hybridized to that portion of the analyte present in that detection volume.

Figure 8:
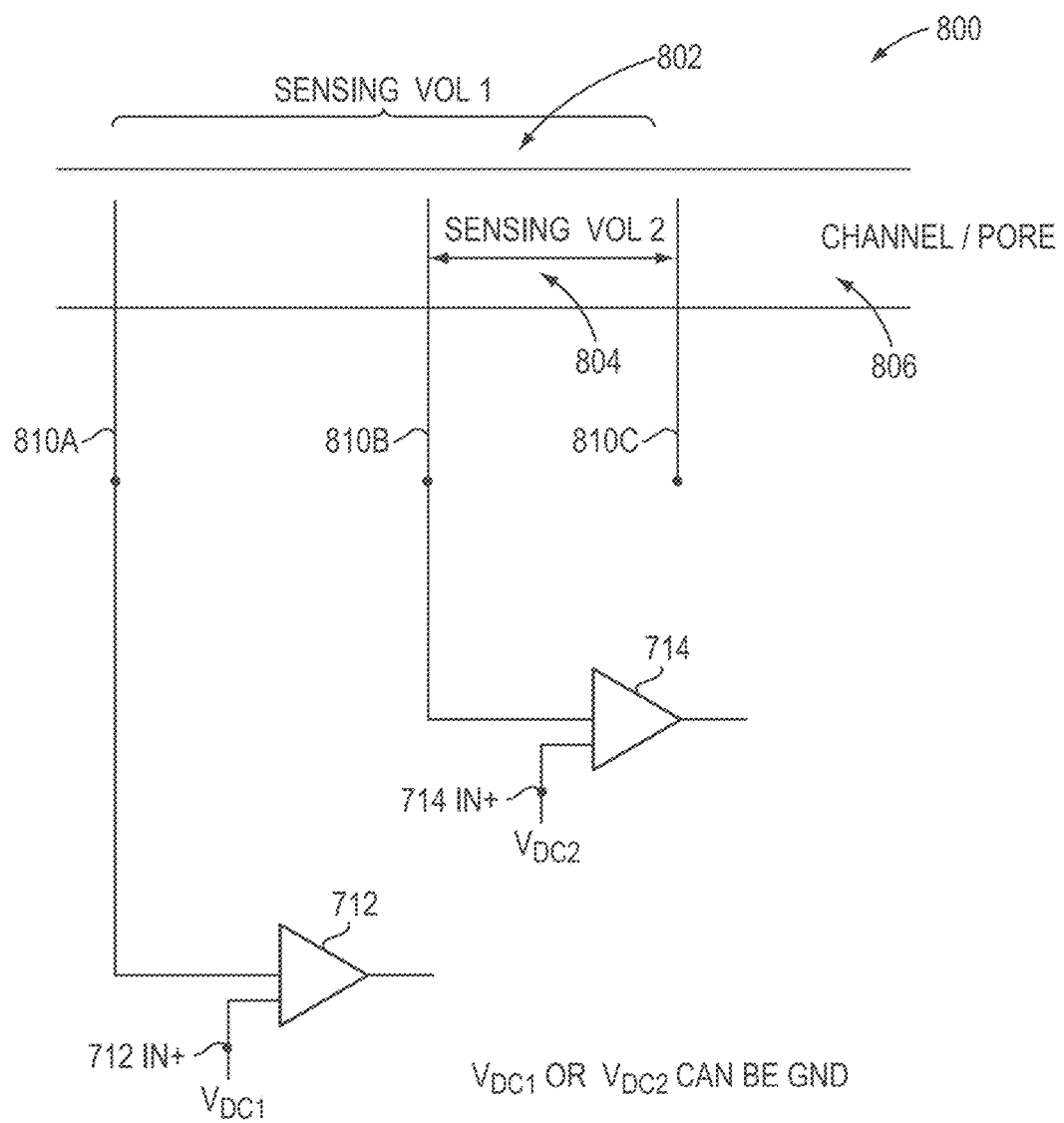
FIG. 8 is a schematic drawing of another embodiment of circuitry for an apparatus with multiple detection volumes, according to another illustrative embodiment of the invention.

FIG. 8 presents an alternative system 800 that also employs two detection volumes 802, 804 in a fluidic channel 806. These detection volumes are defined by the electrodes 810A, 810B, 810C such that the first detection volume 802 overlaps the second detection volume 804. The AC voltage excitation signal may be supplied to both detection volumes 802, 804 via the electrode 810C, and the presence of analyte is detected using the I-to-V converters 712, 714. Instead of using $V_{DC1}$ or $V_{DC2}$, either one of the non-inverting input nodes 712IN+, 714IN+, or both may be connected to ground, as shown with respect to the I-to-V converter 406 of FIG. 4A.

Figure 9A:
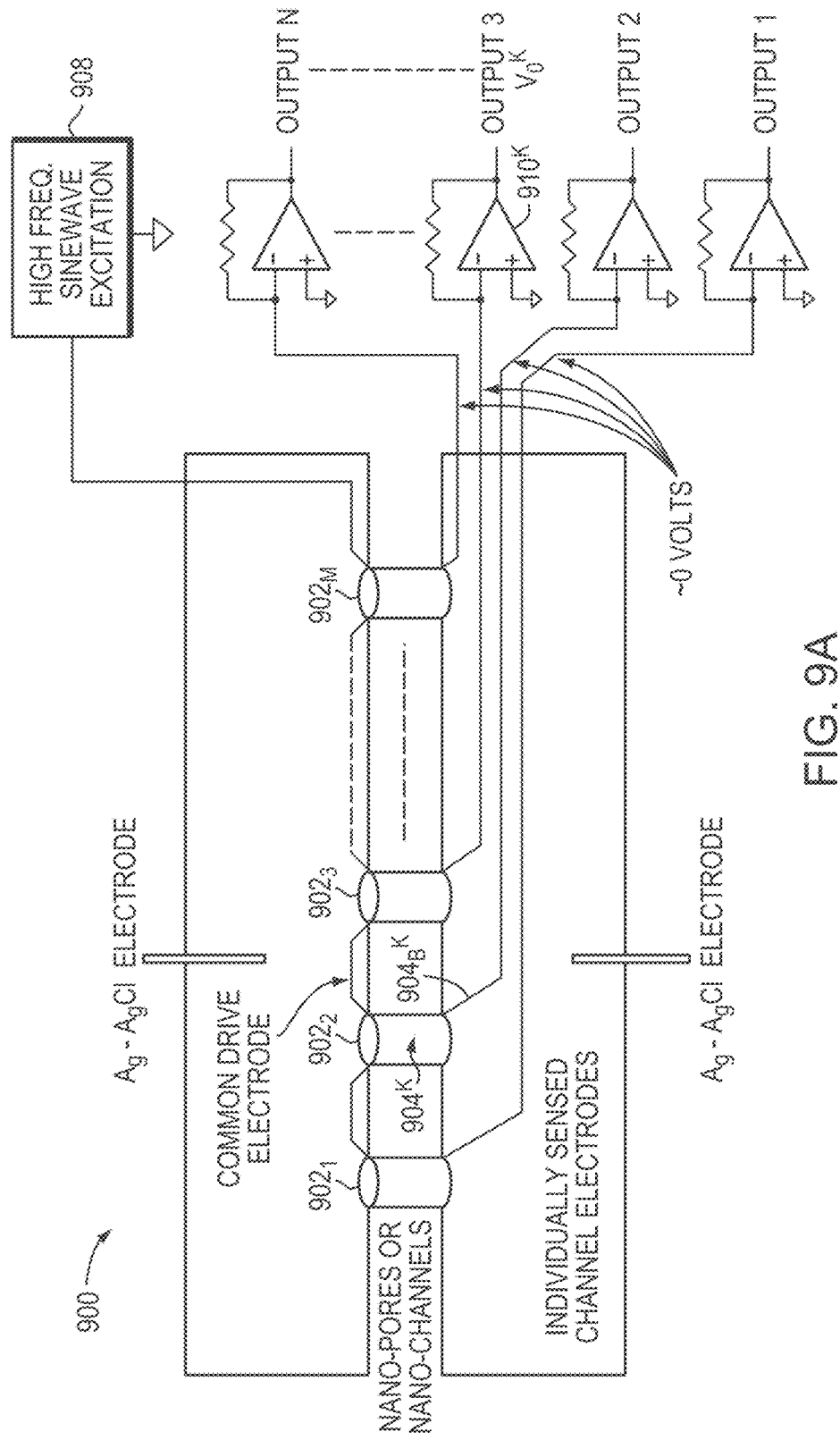
FIG. 9A is a schematic drawing of an apparatus featuring multiple pores or channels and multiplexing circuitry, according to one illustrative embodiment of the invention.
Figure 9B:
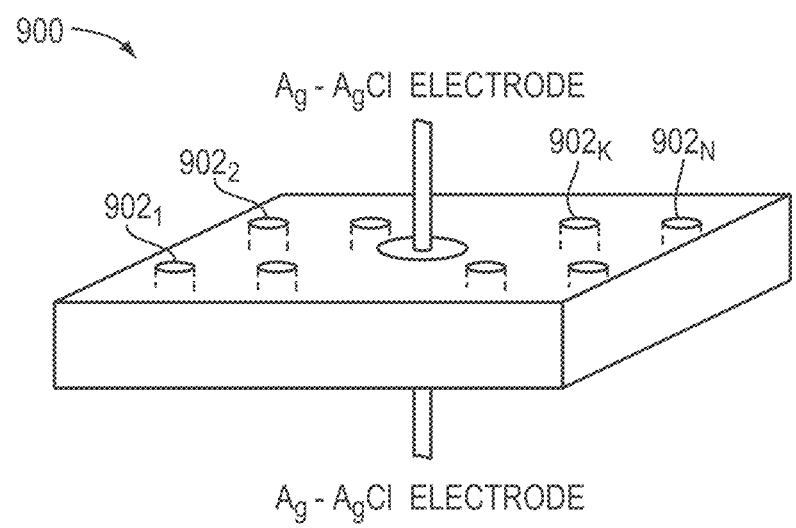
FIG. 9B is a schematic drawing of another embodiment of an apparatus featuring multiple pores or channels configured as a matrix, according to another illustrative embodiment of the invention.
Figure 10A:
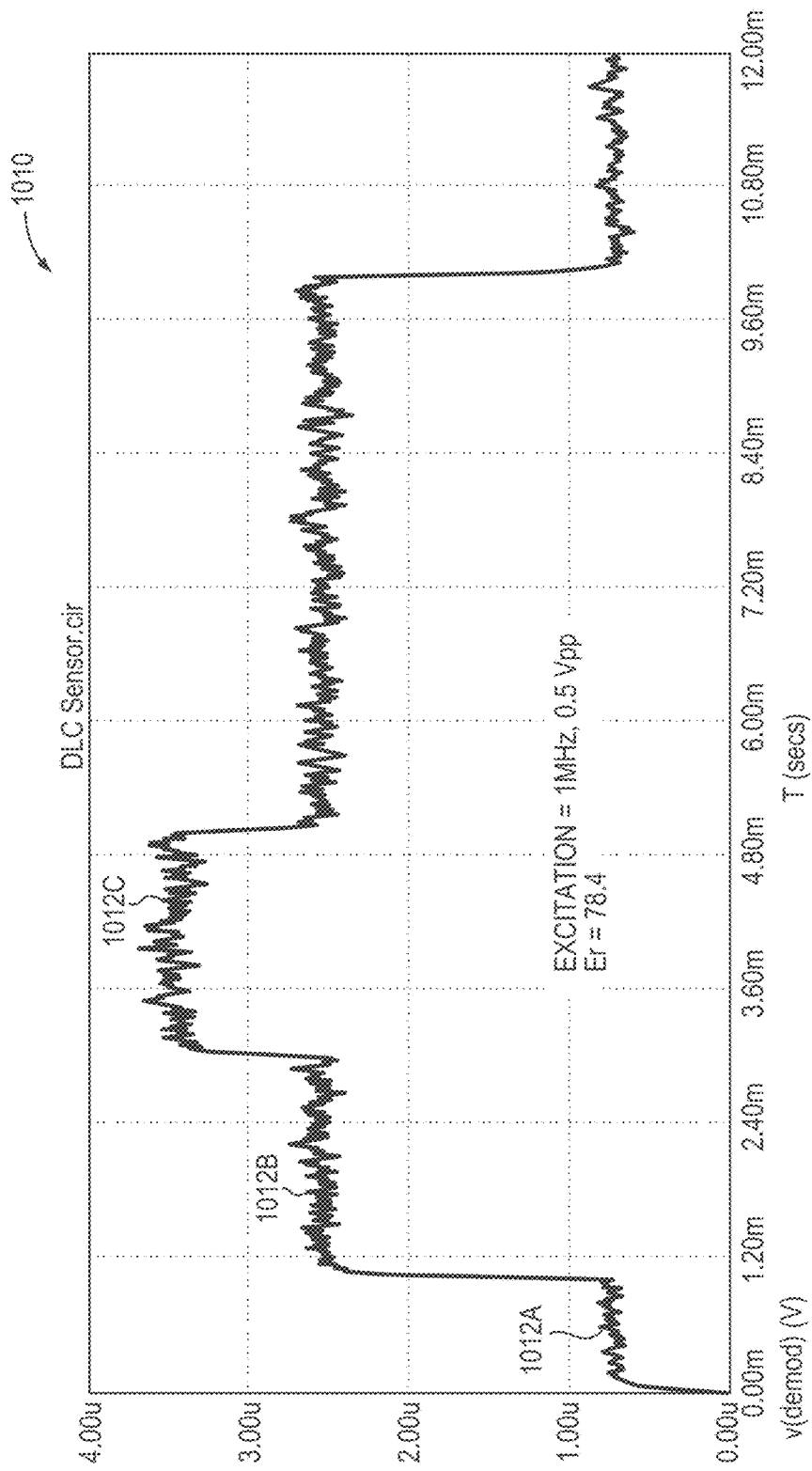
FIGS. 10A-10F depict graphs demonstrating signal-to-noise ratio (SNR) as a function of amplitude of the alternating current (AC) excitation-induced potential across a detection volume, according to an illustrative embodiment of the invention.
Figure 10B:
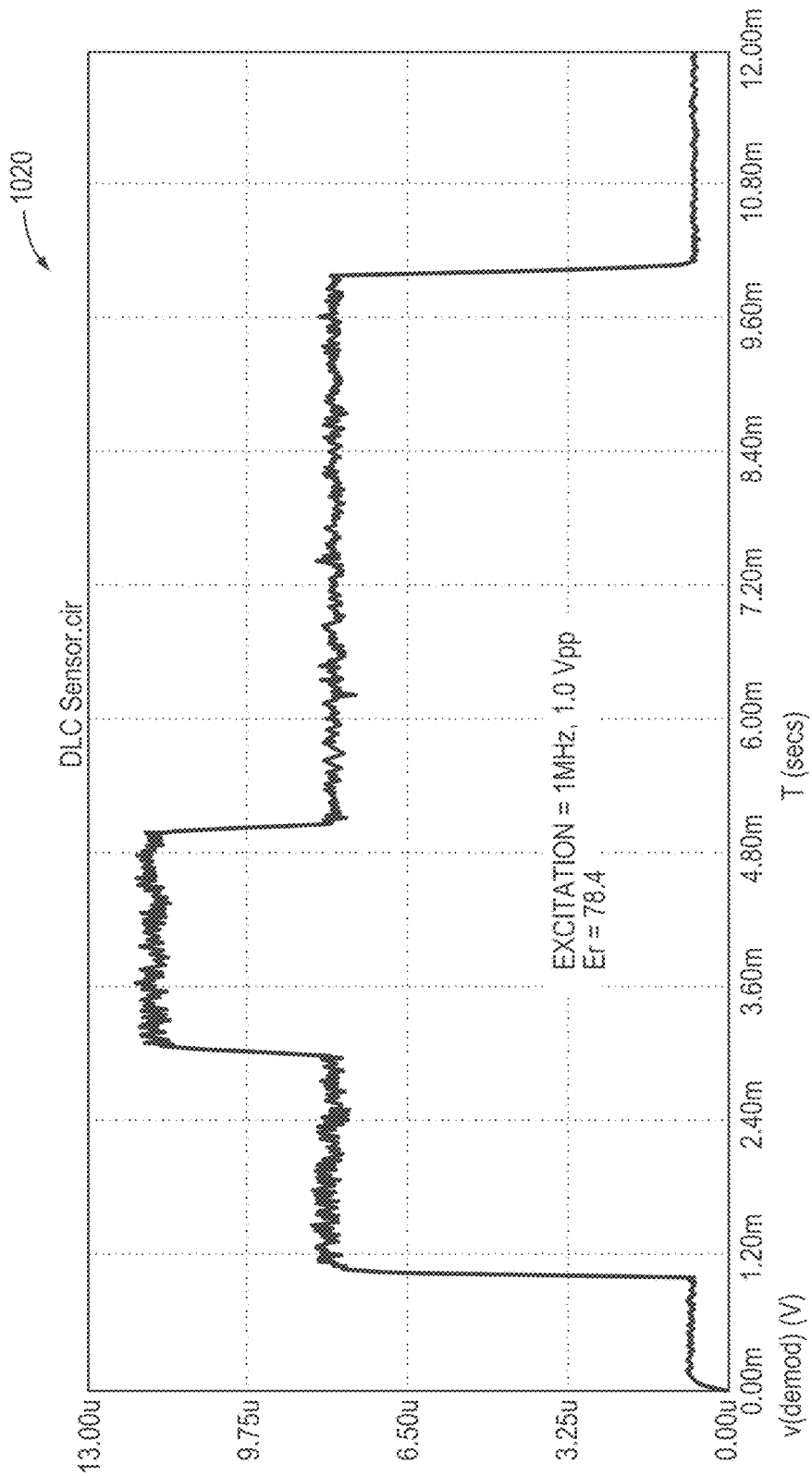
Figure 10C:
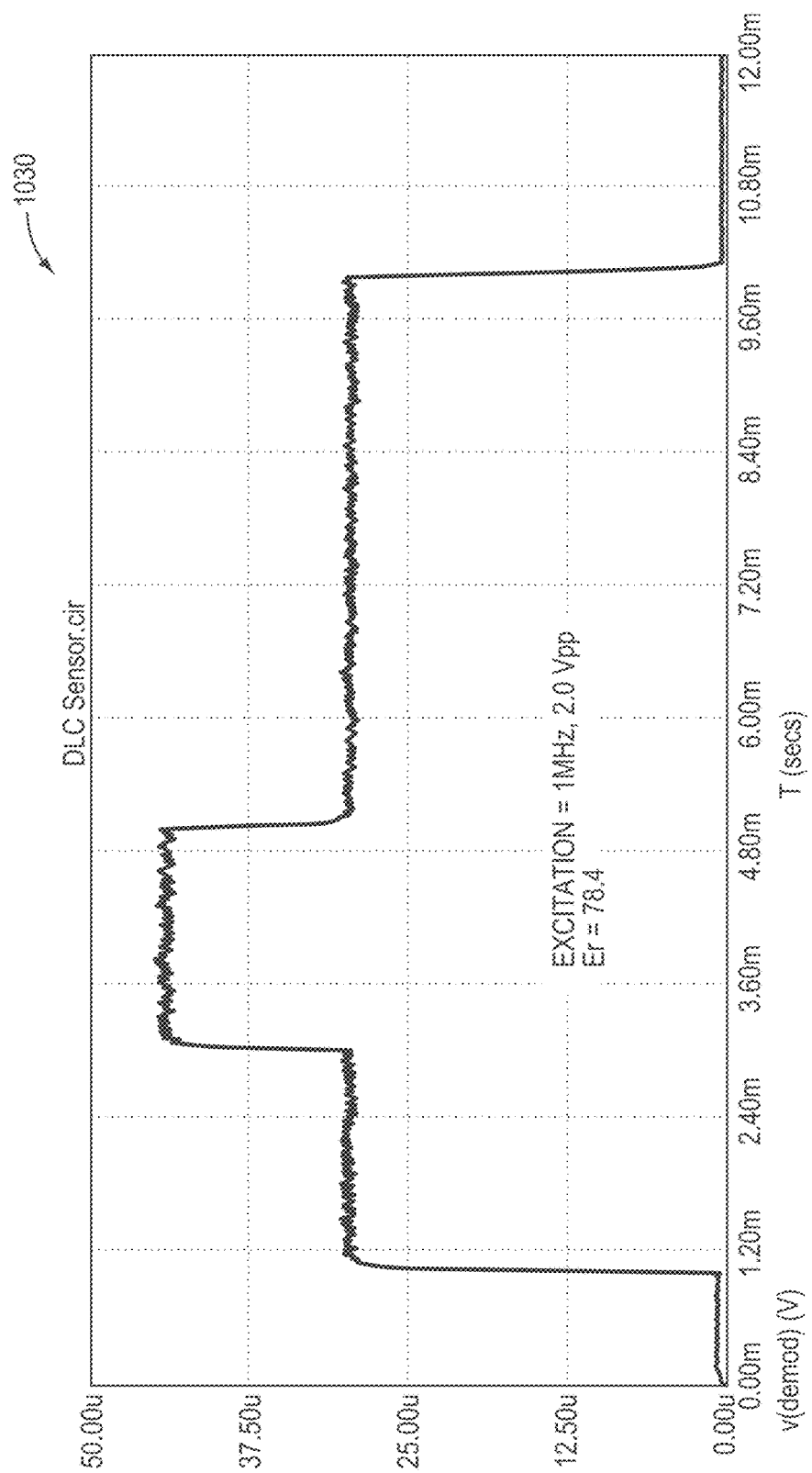
Figure 10D:
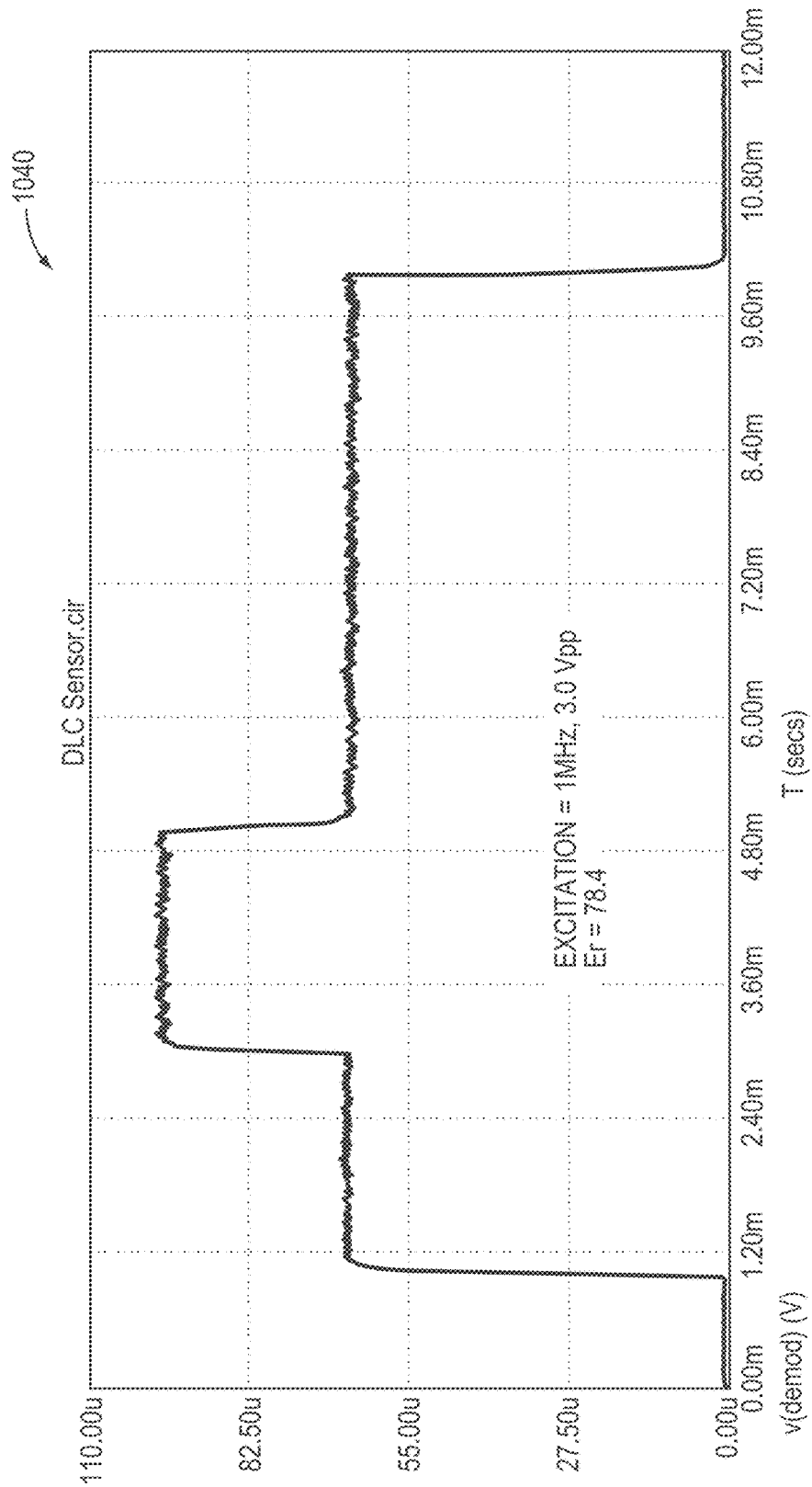
Figure 10E:
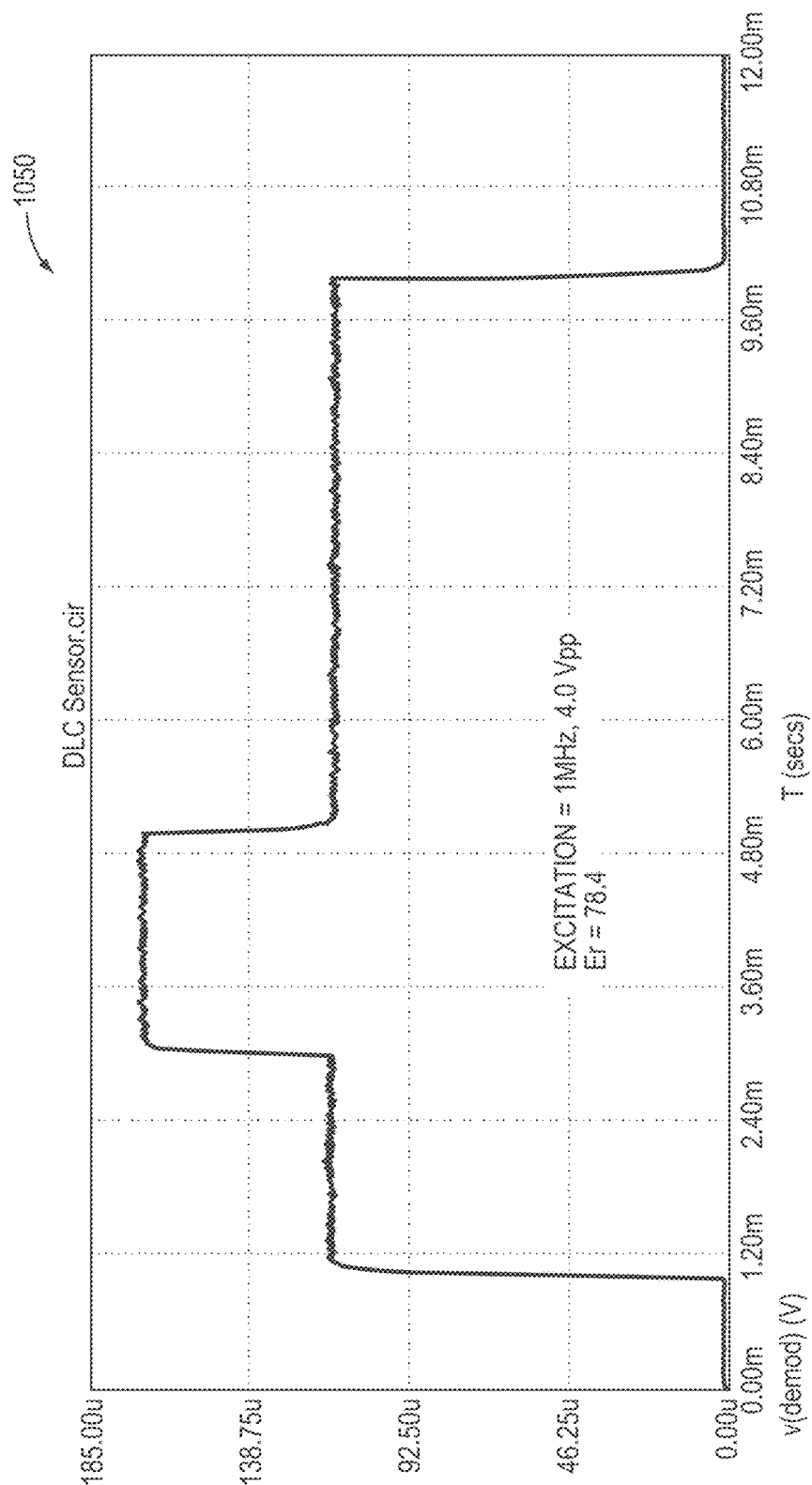
Figure 10F:
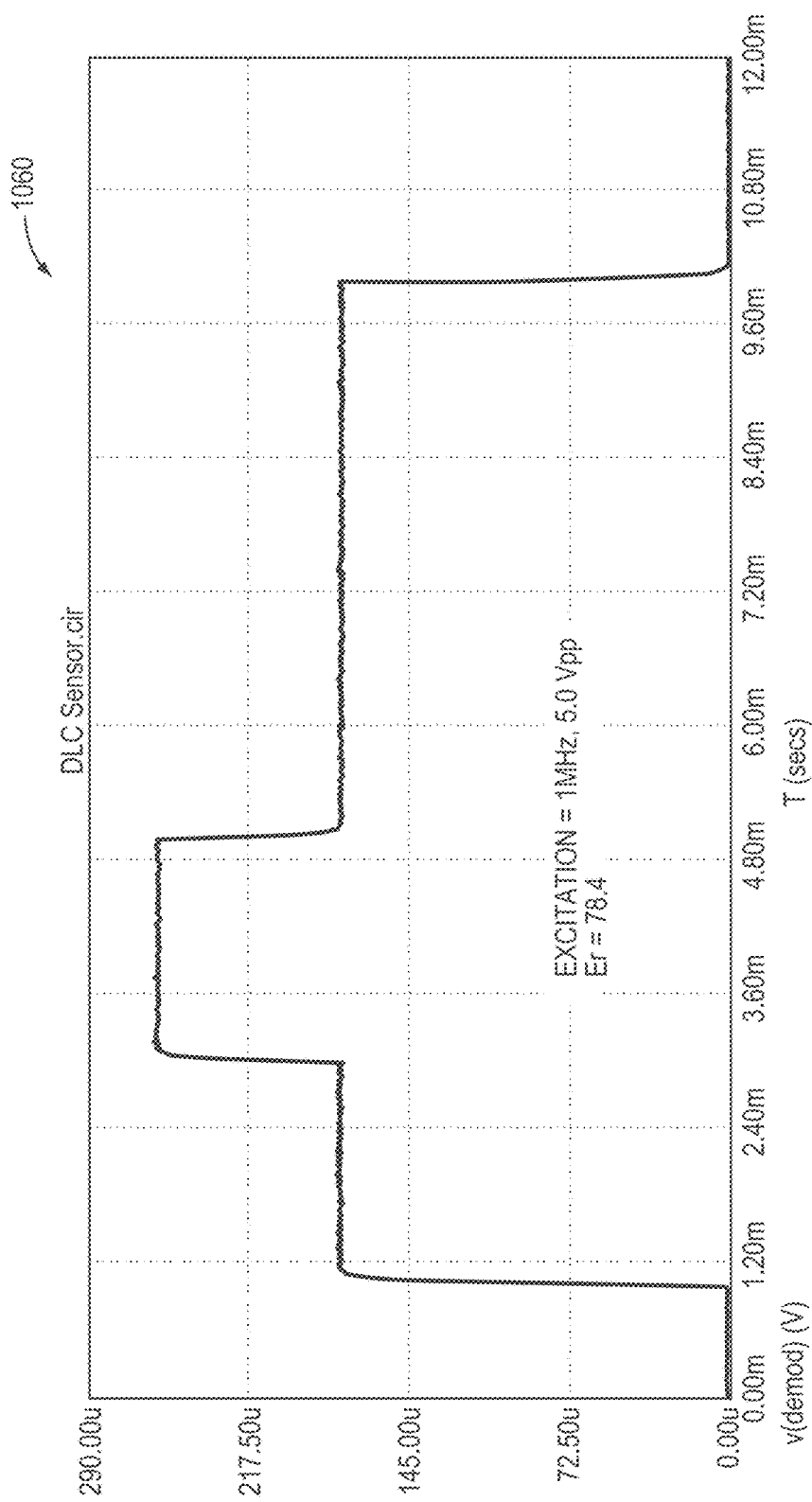

The system 900 depicted in FIG. 9A includes a number of nanopores or micro- or nano-channels, of which four, $902_1$, $902_2$, $902_3$ and $902_N$ are shown. A pair of electrodes $904^k A$, $904^k B$ defines a detection volume $906^k$. Though FIG. 9A shows only one detection volume $906^k$ per pore or channel, in some embodiments, several detection volumes per channel may be defined for one or more pores or channels. Thus, as shown in FIGS. 7 and 8, three or more detector electrodes per pore or channel may be employed. Also, the pores or channels may be arranged in an array, as shown in FIG. 9A, or as a two dimensional matrix, as shown in FIG. 9B.

In the system 900, the electrodes $904^k A$ are in electrical communication with each other and with a high-frequency AC voltage excitation source 908. In alternative embodiments, multiple excitation sources may be used. The electrode $904^k B$ corresponding to the k-th pore or channel is in electrical communication with an I-to-V converter $910^k$. In the system 900 the I-to-V converters $910^k$ are op-amps, and the non-inverting input of each op-amp $910^k$ is connected to ground. In certain embodiments, one or more non-inverting terminals are connected to one or more voltages other than ground (e.g., $V_{DC1}$, $V_{DC2}$, etc.).

As described above with reference to FIG. 4A, the output voltage denoted as $V^k_o$ of each I-to-V converter $910^k$ indicates whether a portion of an analyte is present in the detection volume $906^k$, and whether a probe is hybridized to that detected portion of analyte. Because the same excitation signal is supplied to each detection volume $906^k$, and because the non-inverting terminal of each I-to-V converter $910^k$ is at the same ground potential, there is virtually no "cross-talk" in the system 900. As used herein, cross-talk generally refers to an impact on the detection of an analyte in one pore or channel (e.g., the pore $902_3$) due to the presence of an analyte in another pore or channel (e.g., the pore $902_1$). Cross-talk may cause false detection of an analyte or erroneous detection of its absence. The configuration of the system 900 as described above, however, can mitigate or eliminate errors due to cross talk and facilitate simultaneous, rapid detection of analytes using several pores or channels simultaneously.

With reference to FIGS. 10A-10F, the waveforms 1010, 1020, 1030, 1040, 1050 and 1060 depict a family of computer modeled simulation results detecting (i) no analyte, (ii) analyte with no hybridized probe and (iii) analyte with hybridized probe in a detection volume. e.g., using the system 400. These results correspond to V"o in FIG. 4A. Excitation frequency was assumed to be 1 MHz and each waveform represents a simulation run performed at a different excitation magnitude ranging from 0.5V peak-to-peak to 5.0V peak-to-peak. The electrolytic properties of the fluid were modeled to match the electro-chemical properties of 1 molar KCL. The analyte, modeled to match the properties of RecA coated DNA, is assumed to be electrically non-conductive and its geometric properties, length and radius, were modeled as 50 thousand base pairs and 4.5 nm respectively. The parameters for the nano-channel are 200 nm wide×200 nm deep with a defined sense volume length of 200 nm. The sense volume model also includes a roughly Gaussian noise source approximately equivalent to the thermal noise (also called Johnson noise) of the sense volume resistance as calculated from the assumed nano-channel/sense volume geometry. All of the waveforms clearly illustrate the ability to distinguish between three important states (i) where there is no analyte in the detection volume; (ii) where there is a portion of the analyte lacking a hybridized probe in the detection volume; and (iii) where there is a portion of the analyte having a hybridized probe in the detection volume. The family of results, in aggregate, shows the improvement in signal to noise performance that can be achieved as the excitation amplitude is increased.

Referring to FIG. 10, waveform 1010, the AC excitation signal applied to the detection volume has a frequency of about 1 MHz and peak-to-peak voltage ($V_{pp}$) of about 0.5 V. The waveform 1010 includes three voltage levels: 1012A at about 0.8 µv; 1012B at about 2.5 µv; and 1012C at about 3.5 µv. The level 1012A indicates that an analyte is not present in the detection volume and, as its value is not exactly zero, is representative of the residual error, i.e. imperfections of the baseline subtraction function, and the levels 1012B, 1012C each indicates that the analyte is present. The level 1012C additionally indicates that the analyte portion present in the detection volume includes a hybridized probe.

For waveform 1020, the AC excitation signal applied to the detection volume has a frequency of about 1 MHz and $V_{pp}$ of about 1.0 V. The waveform 1020 includes three voltage levels: ~0.8 µv; ~7.5 µv; and ~12.5 µv. The first level indicates that an analyte is not present in the detection volume and, as its value is not exactly zero, is representative of the residual error, i.e. imperfections of the baseline subtraction function, and the additional levels each indicate that the analyte is present. The level at ~12.5 µv additionally indicates that the analyte portion present in the detection volume includes a hybridized probe.

For waveform 1030, the AC excitation signal applied to the detection volume has a frequency of about 1 MHz and $V_{pp}$ of about 2.0 V. The waveform 1030 includes three voltage levels: ~0.8 µv; ~30 µv; and ~45 µv. The first level indicates that an analyte is not present in the detection volume and, as its value is not exactly zero, is representative of the residual error, i.e. imperfections of the baseline subtraction function, and the additional levels each indicate that the analyte is present. The level at ~45 µv additionally indicates that the analyte portion present in the detection volume includes a hybridized probe.

For waveform 1040, the AC excitation signal applied to the detection volume has a frequency of about 1 MHz and $V_{pp}$ of about 3.0 V. The waveform 1040 includes three voltage levels: ~0.8 µv; ~67 µv; and ~100 µv. The first level indicates that an analyte is not present in the detection volume and, as its value is not exactly zero, is representative of the residual error, i.e. imperfections of the baseline subtraction function, and the additional levels each indicate that the analyte is present. The level at ~100 μv additionally indicates that the analyte portion present in the detection volume includes a hybridized probe.

For waveform 1050, the AC excitation signal applied to the detection volume has a frequency of about 1 MHz and $V_{pp}$ of about 4.0 V. The waveform 1050 includes three voltage levels: ~0.8 μv; ~115 μv; and ~195 μv. The first level indicates that an analyte is not present in the detection volume and, as its value is not exactly zero, is representative of the residual error, i.e. imperfections of the baseline subtraction function, and the additional levels each indicate that the analyte is present. The level at ~195 μv additionally indicates that the analyte portion present in the detection volume includes a hybridized probe.

For waveform 1060, the AC excitation signal applied to the detection volume has a frequency of about 1 MHz and $V_{pp}$ of about 5.0 V. The waveform 1060 includes three voltage levels: ~0.8 μv; ~170 μv; and ~265 μv. The first level indicates that an analyte is not present in the detection volume and, as its value is not exactly zero, is representative of the residual error, i.e. imperfections of the baseline subtraction function, and the additional levels each indicate that the analyte is present. The level at ~265 μv additionally indicates that the analyte portion present in the detection volume includes a hybridized probe.

The collection of waveforms discussed above demonstrates that when the excitation magnitude is increased, the signal response at the second and third levels increases faster than the noise, thereby demonstrating an improved Signal-to-Noise ratio. It should be noted as well that in each case, resident noise (indicated by fluctuations at each level) becomes less significant on each waveform with increasing excitation magnitude. The relative increase in the difference between the successive voltage levels can increase the robustness of the detection of the absence or presence of analytes in a detection volume, and that of the determination of whether probes are hybridized to the detected analytes. Moreover, increasing the peak-to-peak voltage of the excitation signal does not noticeably affect the translocation of the analytes in the fluidic channel or pore.

Figure 11:
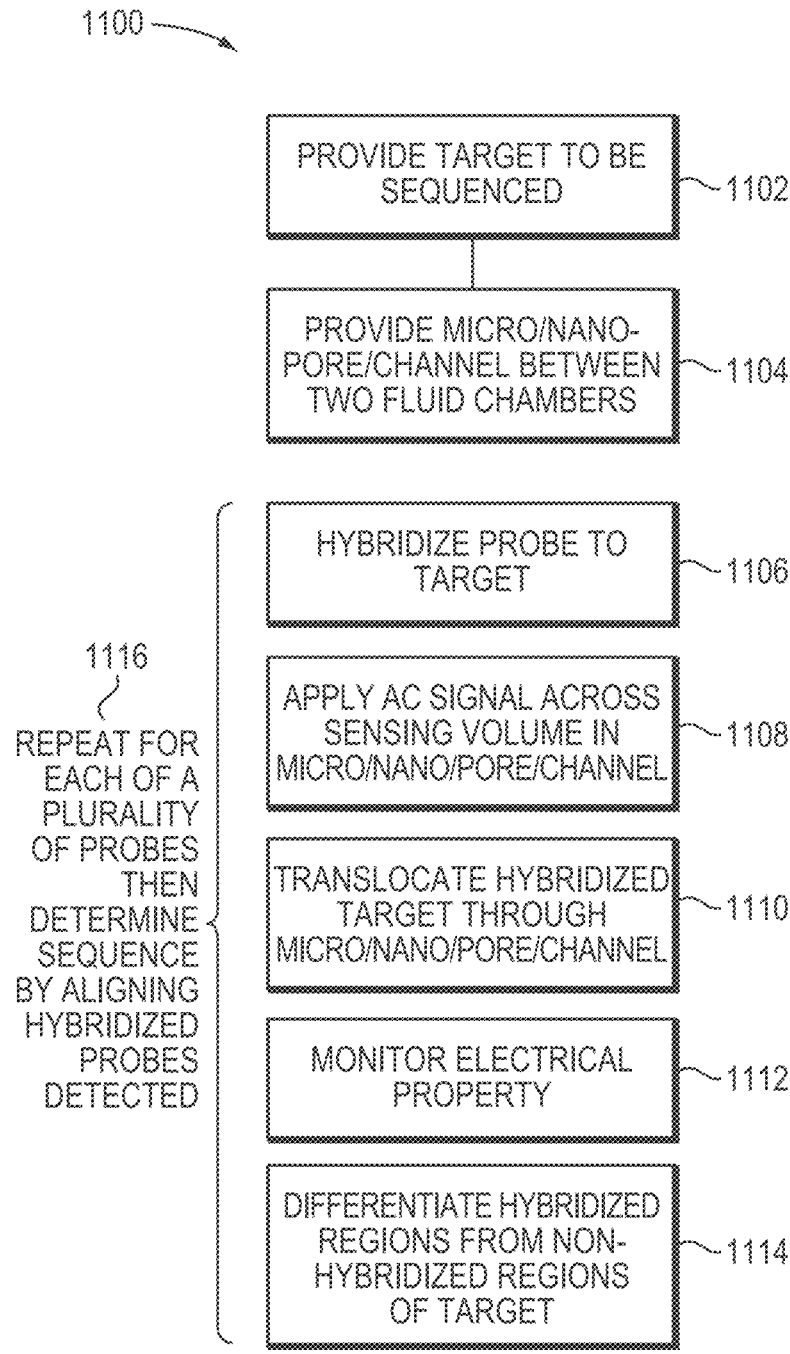
FIG. 11 is a flowchart depicting a method for analyzing a biomolecule, according to an illustrative embodiment of the invention.

FIG. 11 is flowchart 1100 depicting a method for mapping or determining a sequence of a biomolecule analyte. In step 1102, a target biomolecule is provided. In step 1104, an apparatus having first and second fluid chambers in fluid communication with one another is provided, where the first and second fluid chambers are separated by a structure defining a micropore, a nanopore, a microchannel, and/or a nanochannel, and wherein the apparatus includes at least one pair of electrodes defining at least one detection volume within the structure.

In step 1106 a first probe set comprising a plurality of probes identical in sequence and length is hybridized to a first sample of the target biomolecule to provide a target biomolecule analyte having first probes hybridized to complementary regions thereon. In certain embodiments, the target analyte is coated with one or more proteins to enhance the detectability of the analyte as it passes through the detection volume. In certain embodiments, the probe may include a tag to increase its size and enhance the detectability of the probe as it passes through the detection volume.

In step 1108 an alternating current (AC) voltage excitation signal is applied across one or more of the at least one detection volumes.

In step 1110 the target analyte is translocated through the at least one detection volume, for example, using a pair of electrodes located at the ends of the channel or pore that provides an electromotive force to propel the analyte through the channel or pore.

In step 1112 an electrical property detected in the detection volume is monitored, and step 1114 then determines, as a function of time, (i) when there is no analyte in the detection volume; (ii) when there is a portion of the analyte lacking a hybridized probe in the detection volume; and (iii) when there is a portion of the analyte having a hybridized probe in the detection volume. Embodiments of steps 1110, 1112, and 1114 are described in more detail herein, for example, with respect to the devices of FIGS. 3-9.

Steps 1106 through 1114 are repeated for each of a plurality of additional probes attached to the target biomolecule (e.g., duplicates thereof), either using one probe (type) at a time, or multiple distinguishable probes at a time. The data may be analyzed by one of a number of software algorithms to align the detected probe and identify the sequence of the corresponding target (or desired portion thereof). Furthermore, the devices and systems described herein can be used to execute one or more steps of the method of FIG. 11.

Figure 12:
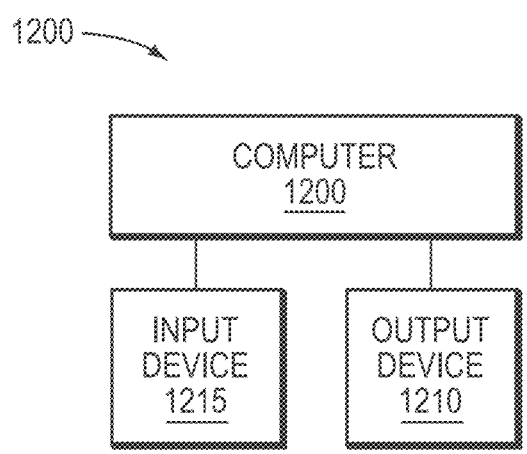
FIG. 12 is a schematic drawing of a computer and associated input/output devices, according to one illustrative embodiment of the invention.

FIG. 12 is a schematic drawing 1200 of a computer and associated input/output devices, per certain embodiments of the invention. The computer 1205 in FIG. 12 can be a general purpose computer, such as a commercially available personal computer that includes a CPU, one or more memories, one or more storage media, one or more output devices 1210, such as a display, and one or more user input devices 1215, such as a keyboard. The computer operates using any commercially available operating system, such as any version of the Windows™ operating systems from Microsoft Corporation of Redmond, Wash., or the Linux™ operating system from Red Hat Software of Research Triangle Park, N.C. The computer is programmed with software including commands that, when operating via a processor, direct the computer in the performance of the methods of embodiments of the invention. Those of skill in the programming arts will recognize that some or all of the commands can be provided in the form of software, in the form of programmable hardware such as flash memory, ROM, or programmable gate arrays (PGAs), in the form of hard-wired circuitry, or in some combination of two or more of software, programmed hardware, or hard-wired circuitry. Commands that control the operation of a computer are often grouped into units that perform a particular action, such as receiving information, processing information or data, and providing information to a user. Such a unit can comprise any number of instructions, from a single command, such as a single machine language instruction, to a plurality of commands, such as a plurality of lines of code written in a higher level programming language such as C++. Such units of commands are referred to generally as modules, whether the commands include software, programmed hardware, hard-wired circuitry, or a combination thereof. The computer and/or the software includes modules that accept input from input devices, that provide output signals to output devices, and that maintain the orderly operation of the computer. In certain embodiments, the computer 205 is a laptop computer, a minicomputer, a mainframe computer, an embedded computer, or a handheld computer. The memory is any conventional memory such as, but not limited to, semiconductor memory, optical memory, or magnetic memory. The storage medium is any conventional machine-readable storage medium such as, but not limited to, floppy disk, hard disk, CD-ROM, and/or magnetic tape. The one or more output devices 1210 may include a display, which can be any conventional display such as, but not limited to, a video monitor, a printer, a speaker, and/or an alphanumeric display. The one or more input devices 1215 may include any conventional input device such as, but not limited to, a keyboard, a mouse, a touch screen, a microphone, and/or a remote control. The computer 1205 can be a stand-alone computer or interconnected with at least one other computer by way of a network. This may be an internet connection.

In certain embodiments, the computer 1205 in FIG. 12 includes and/or runs software for determining a sequence of a biomolecule (e.g., DNA) from input data, according to the methods described herein. In certain embodiments, one or more modules of the software may be run on a remote server, e.g., the user may access and run the software via the internet.

EQUIVALENTS

While the invention has been particularly shown and described with reference to specific preferred embodiments, it should be understood by those skilled in the art that various embodiments are provided by way of example only, and that changes in form or detail may be made therein without departing from the spirit and scope of the invention as defined by the appended claims.

What is claimed is:

1. A device for analyzing a target biomolecule, the device comprising:
   a substrate defining a fluidic channel or pore;
   a driving force generator adapted to drive a target biomolecule analyte through said fluidic channel or pore, said analyte comprising a biomolecule having at least one region including a hybridized probe and at least one region lacking a hybridized probe;
   a plurality of detector electrodes disposed in relation to the fluidic channel or pore to define at least one detection volume in the fluidic channel or pore, the detection volume being defined by a pair of the detector electrodes laterally offset from each other along the fluidic channel or pore, one detector electrode of the plurality of detector electrodes detecting current that produces a detection volume output signal;
   an excitation source for supplying an AC voltage excitation signal to the at least one detection volume and to a reference generator producing a reference signal distinct from the detection volume output signal; and
   detection circuitry for producing a sensor signal associated with the at least one detection volume, the detection circuitry comprising the reference generator, and the sensor signal being based on a comparison of the detection volume output signal with the reference signal,
   wherein the sensor signal is indicative of (i) the absence of the analyte in a detection volume, (ii) the presence of a portion of the analyte lacking a hybridized probe in the detection volume, and (iii) the presence of a portion of the analyte having a hybridized probe in the detection volume.

2. The device of claim 1, wherein the driving force generator comprises at least two electromotive electrodes disposed at opposing ends of said fluidic channel or pore, said electromotive electrodes configured to apply a DC potential for translocation of the analyte through said fluidic channel or pore.

3. The device of claim 2, wherein the circuitry is configured such that the AC voltage excitation signal is superpositioned over the DC potential.

4. The device of claim 1, wherein the driving force generator comprises at least one of electrical potential, a fluidic pressure differential, a chemical potential gradient, osmotic pressure, or combinations thereof.

5. The device of claim 1, wherein the AC signal is a high frequency AC voltage excitation signal that has frequency in a range from about 10 kHz to about 50 MHz.

6. The device of claim 5, wherein the AC signal has a frequency in a range from about 10 kHz to about 5.5 MHz.

7. The device of claim 5, wherein the AC signal has a frequency in a range from about 5 MHz to about 50 MHz.

8. The device of claim 1, wherein the circuitry comprises:
   a reference signal generator for generating a reference signal representative of a steady-state baseline; and
   a subtractor for generating a difference signal by subtracting the reference signal from the sensor signal, wherein a value of the difference signal is
   (i) approximately zero in response to the absence of the analyte in a detection volume,
   (ii) a voltage $V_2$ in response to the presence of a portion of the analyte lacking the hybridized probe in the detection volume, and
   (iii) a voltage $V_3$ in response to the presence of a portion of the analyte that includes the hybridized probe in the detection volume,
   wherein $V_3 > V_2 > 0$.

9. The device of claim 8, wherein the reference signal generator develops a signal that is substantially equal to and continuously tracks the steady-state background signal and comprises a controller for adjusting at least one of an amplitude and a phase of the reference signal.

10. The device of claim 9, wherein the controller is configured to adjust at least one of the amplitude and the phase of the reference signal such that if the analyte is not present within the detection volume, the difference signal is approximately 0 volts.

11. The device of claim 1, wherein the sensor signal is a detectable current.

12. The device of claim 11, further comprising a first current-to-voltage converter for converting the sensor signal into an AC voltage signal having voltage related to the current of the sensor signal.

13. The device of claim 12, wherein the first current-to-voltage converter is an operational amplifier having a first input connected to one of the detector electrodes, and a second input connected to a ground potential.

14. The device of claim 12, wherein the first current-to-voltage converter is an operational amplifier having a first input connected to one of the detector electrodes, and a second input connected to a potential (VDC1) relative to a ground potential.

15. The device of claim 11, wherein the plurality of detector electrodes disposed in relation to the fluidic channel or pore define a plurality of detection volumes in the fluidic channel or pore, the device further comprising:
   a first operational amplifier having a first input connected to a first sensing electrode, and a second input connected to a first potential; and
   a second operational amplifier having a first input connected to a second sensing electrode, and a second input connected to a second potential.

16. The device of claim 15, wherein at least one of the first and second potentials is a ground potential.

17. The device of claim 12, wherein the circuitry comprises:
   a reference signal generator for generating a reference signal;

a second current-to-voltage converter for converting the reference signal into a reference AC voltage signal; and a subtractor for generating a difference voltage signal by subtracting the reference AC voltage signal from the AC voltage signal, wherein magnitude of the difference voltage signal is indicative of (i) absence of the analyte in a detection volume, (ii) presence of a portion of the analyte lacking a hybridized probe in the detection volume, and (iii) presence of a portion of the analyte having a hybridized probe in the detection volume.

18. The device of claim 17, wherein the circuitry comprises a demodulator for demodulating the difference voltage signal to obtain a demodulated difference signal, the demodulated difference signal being indicative of (i) absence of the analyte in a detection volume, (ii) presence of a portion of the analyte lacking a hybridized probe in the detection volume, and (iii) presence of a portion of the analyte having a hybridized probe in the detection volume.

19. The device of claim 12, wherein the circuitry comprises a demodulator for demodulating the AC voltage signal to obtain a demodulated signal, wherein the demodulated signal is indicative of (i) absence of the analyte in a detection volume, (ii) presence of a portion of the analyte lacking a hybridized probe in the detection volume, and (iii) presence of a portion of the analyte having a hybridized probe in the detection volume.

20. The device of claim 1, wherein the sensor signal is a detectable voltage.

21. The device of claim 20, wherein the pair of detector electrodes comprises a first sensing electrode and a second sensing electrode and wherein the circuitry comprises:
    a first current-to-voltage converter in electrical communication with the first sensing electrode; and
    a second current-to-voltage converter in electrical communication with the second sensing electrode,
    wherein the sensor signal comprises a difference between voltages produced by the first and second current-to-voltage converters.

22. The device of claim 1, wherein the circuitry comprises:
    a demodulator for converting the sensor signal into a DC signal; and
    a subtractor for subtracting a DC reference signal from the DC signal, thereby producing a DC difference signal, wherein the DC difference signal is indicative of (i) absence of the analyte in a detection volume, (ii) presence of a portion of the analyte lacking a hybridized probe in the detection volume, and (iii) presence of a portion of the analyte having a hybridized probe in the detection volume.

23. The device of claim 1, wherein the fluidic channel or pore comprises a nanochannel, a microchannel, a nanopore, or a micropore.

24. The device of claim 1, wherein the substrate defines a plurality of fluidic channels or pores, each of the fluidic channels or pores having a plurality of detector electrodes disposed in relation to its respective fluidic channel or pore to define one or more detection volumes in the fluidic channel or pore.

25. The device of claim 24, wherein each fluidic channel or pore has (a) a first current-to-voltage converter in electrical communication with a first detection volume of its respective fluidic channel or pore, the converter producing a sensor signal, and (b) a detector configured to detect the sensor signal as a function of time,
    wherein the sensor signal is indicative of (i) the absence of the analyte in a first detection volume, (ii) the presence of a portion of the analyte lacking a hybridized probe in the first detection volume, and (iii) the presence of a portion of the analyte having a hybridized probe in the first detection volume.

26. The device of claim 25, wherein the first current-to-voltage converter is an operational amplifier having a first input connected to one electrode which, in part, defines the first detection volume, and a second input connected to a first potential (VDC1).

27. The device of claim 25, wherein at least one of the fluidic channels or pores, comprises a plurality of detector electrodes defining a plurality of detection volumes in the fluidic channel or pore, the system further comprising:
    a first operational amplifier having a first input connected to a first sensing electrode and a second input connected to a first potential VDC1; and
    a second operational amplifier having a first input connected to a second sensing electrode, and a second input connected to a second potential VDC2.

28. The device of claim 27, wherein at least one of the first and second potentials is a ground potential.

29. A method for sequencing a target biomolecule, the method comprising:
    (a) providing a target biomolecule;
    (b) providing an apparatus having first and second fluid chambers in fluid communication with one another, wherein the first and second fluid chambers are separated by a structure defining a micropore, a nanopore, a microchannel, and/or a nanochannel, and wherein the apparatus includes a plurality of detector electrodes defining at least one detection volume within the structure;
    (c) hybridizing a first probe set comprising a plurality of probes identical in sequence and length to a first sample of the target biomolecule to provide a first hybridized biomolecule analyte having first probes hybridized to complementary regions thereon;
    (d) optionally, at least partially coating the first analyte with one or more proteins;
    (e) applying an alternating current voltage excitation signal obtained from an excitation source across at least one detection volume;
    (f) translocating the first analyte through the at least one detection volume;
    (g) monitoring via the electrodes defining the at least one detection volume, as a function of time, an electrical property as the first analyte translocates therethrough, wherein one of the electrodes detects current that produces a detection volume output signal, the monitoring comprising:
        obtaining a sensor signal associated with the at least one detection volume, the sensor signal being produced, at least in part, by a detection circuitry comprising a reference generator producing a reference signal distinct from the detection volume output signal, wherein the excitation source provides the excitation signal to the reference generator, and the sensor signal is based on, at least in part, a comparison of the detection volume output signal with the reference signal; and
        detecting based on the sensor signal at least one of: (i) the absence of the analyte in a detection volume, (ii) the presence of a portion of the analyte lacking a hybridized probe in the detection volume, and (iii) the presence of a portion of the analyte in the detection volume, that portion having a hybridized probe;

(h) differentiating between hybridized and non-hybridized regions of the first analyte based at least in part on detected changes in the electrical property in the at least one detection volume;

(i) sequencing at least a portion of the target biomolecule based at least in part on the hybridized and non-hybridized regions differentiated in step (h).

30. The method of claim 29, further comprising:

after step (c) or after step (f), (i) hybridizing a second probe set to the first sample of the target biomolecule or, alternatively, a second sample of the target biomolecule, wherein the second probe set comprises a plurality of probes of identical sequence and length that are different from the probes in the first probe set, (ii) translocating the biomolecule hybridized with the second probe through the at least one detection volume, wherein the differentiation step comprises differentiating between regions of the target biomolecule hybridized with the second probe and non-hybridized regions of the target biomolecule, based at least in part on the detected changes in the electrical property in the at least one detection volume, and wherein the sequencing step comprises sequencing at least a portion of the target biomolecule based at least in part on the differentiated hybridized and non-hybridized regions.

31. The method of claim 30, wherein both the first probe set and the second probe set are hybridized to the first sample of the target biomolecule, and wherein the method further comprises differentiating between regions of the target biomolecule hybridized by the first probe and regions hybridized by the second probe.

32. The method of claim 29, wherein the AC voltage excitation signal is applied to the at least one detection volume via one or more of the plurality of detector electrodes.

33. The method of claim 32, further comprising supplying the AC voltage excitation signal through a first electrode of the plurality of detector electrodes.

34. The method of claim 33, further comprising receiving the sensor signal from a second electrode of the plurality of detector electrodes, wherein the sensor signal is an AC current signal, and the method comprises converting the AC current signal into an observed voltage signal.

* * * * *